US008822147B2

(12) United States Patent
Sood et al.

(10) Patent No.: US 8,822,147 B2
(45) Date of Patent: *Sep. 2, 2014

(54) SEQUENTIAL ANALYSIS OF BIOLOGICAL SAMPLES

(75) Inventors: Anup Sood, Clifton Park, NY (US); Michael Christopher Montalto, Brielle, NJ (US); Michael Gerdes, Albany, NY (US); Maximilian Lewis Seel, Boston, MA (US); Robert John Filkins, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/457,531

(22) Filed: Apr. 27, 2012

(65) Prior Publication Data

US 2012/0231967 A1 Sep. 13, 2012

Related U.S. Application Data

(60) Continuation of application No. 12/611,299, filed on Nov. 3, 2009, which is a division of application No. 11/560,599, filed on Nov. 16, 2006, now Pat. No. 7,629,125.

(51) Int. Cl.
| | | |
|---|---|---|
| C12Q 1/68 | (2006.01) | |
| G01N 33/58 | (2006.01) | |
| G01N 33/542 | (2006.01) | |
| G01N 33/53 | (2006.01) | |

(52) U.S. Cl.
CPC .............. *G01N 33/53* (2013.01); *G01N 33/582* (2013.01); *G01N 33/542* (2013.01); *C12Q 1/68* (2013.01)
USPC .......................................................... 435/6.1

(58) Field of Classification Search
None
See application file for complete search history.

(56) References Cited

U.S. PATENT DOCUMENTS

| | | | |
|---|---|---|---|
| 4,405,720 A | 9/1983 | Merril | |
| 5,571,643 A | 11/1996 | Martin et al. | |
| 5,756,709 A | 5/1998 | Nelson et al. | |
| 5,763,152 A | 6/1998 | Hioki et al. | |
| 5,827,656 A | 10/1998 | Nelson et al. | |
| 6,068,979 A * | 5/2000 | Akhavan-Tafti | 435/6.11 |
| 6,083,486 A | 7/2000 | Weissleder et al. | |
| 6,150,173 A | 11/2000 | Schubert | |
| 6,391,649 B1 | 5/2002 | Chait et al. | |
| 6,534,041 B1 | 3/2003 | Licha et al. | |
| 6,573,043 B1 | 6/2003 | Cohen et al. | |
| 6,833,246 B2 | 12/2004 | Balasubramanian | |
| 6,924,115 B2 | 8/2005 | Schubert | |
| 7,629,125 B2 * | 12/2009 | Sood et al. | 435/6.16 |
| 7,741,045 B2 * | 6/2010 | Gerdes et al. | 435/6.16 |
| 7,741,046 B2 * | 6/2010 | Larsen et al. | 435/6.16 |
| 2001/0039023 A1 | 11/2001 | Schubert et al. | |
| 2002/0106648 A1 | 8/2002 | Lizardi et al. | |
| 2002/0116132 A1 | 8/2002 | Rhett et al. | |
| 2002/0173053 A1 | 11/2002 | Damaj et al. | |
| 2002/0177149 A1 | 11/2002 | Rimm et al. | |
| 2003/0044353 A1 | 3/2003 | Weissleder et al. | |
| 2003/0064398 A1 | 4/2003 | Barnes | |
| 2003/0073149 A1 | 4/2003 | Archer et al. | |
| 2004/0121352 A1 | 6/2004 | Dale et al. | |
| 2004/0121382 A1 | 6/2004 | Liu et al. | |
| 2004/0248325 A1 | 12/2004 | Bukusoglu | |
| 2005/0169843 A1 | 8/2005 | Weissleder et al. | |
| 2005/0171434 A1 | 8/2005 | Madden et al. | |
| 2005/0233437 A1 | 10/2005 | Kureshy et al. | |
| 2007/0099208 A1 * | 5/2007 | Drmanac et al. | 435/6 |

FOREIGN PATENT DOCUMENTS

| | | | |
|---|---|---|---|
| DE | 4421891 | A1 | 1/1996 |
| DE | 10143757 | A1 | 3/2003 |
| EP | 153873 | A2 | 9/1985 |
| EP | 0801306 | A1 | 10/1997 |
| FR | 2711671 | A1 | 5/1995 |
| JP | 10503841 | A | 4/1998 |
| JP | 11510681 | A | 9/1999 |
| JP | 2000009732 | A | 1/2000 |
| JP | 2002520448 | A | 7/2002 |
| JP | 2002527404 | A | 8/2002 |
| JP | 2002323416 | A | 11/2002 |
| JP | 2002350431 | A | 12/2002 |
| JP | 2003533209 | A | 11/2003 |
| JP | 2004041121 | A | 2/2004 |
| JP | 2005083942 | A | 3/2005 |

(Continued)

OTHER PUBLICATIONS

Walter Schubert et al., "Analyzing proteome topology and function by automated multidimensional fluorescence microscopy", Nature Biotechnology, vol. 24, pp. 1270-1278, 2006.

Walter Schubert, "Multiple Antigen-Mapping Microscopy of Human Tissue", Advances in analytical Cellular Pathology, Proceedings of the first Conference of the European Society for Analytical Cellular Pathology, pp. 97-98, 1990.

Search Report and Written Opinion from PCT Application No. PCT/US2007/084791 dated Nov. 25, 2008.

(Continued)

*Primary Examiner* — Kenneth R. Horlick
*Assistant Examiner* — David Thomas
(74) *Attorney, Agent, or Firm* — Eileen B. Gallagher

(57) ABSTRACT

Methods for detecting multiple targets in a biological sample are provided. The methods includes contacting the sample with a first probe; physically binding the first probe to a first target; observing a first signal from the first probe; applying a chemical agent to modify the first signal; contacting the sample with a second probe; physically binding the second probe to a second target; and observing a second signal from the second probe. The methods disclosed herein also provide for multiple iterations of binding, observing, signal modification for deriving information about multiple targets in a single sample. An associated kit and device are also provided.

3 Claims, 28 Drawing Sheets

(56) References Cited

FOREIGN PATENT DOCUMENTS

| | | |
|---|---|---|
| JP | 2005261236 A | 9/2005 |
| JP | 200642641 A | 2/2006 |
| JP | 2006513398 A | 4/2006 |
| JP | 2007033159 A | 2/2007 |
| JP | 2010520989 A | 6/2010 |
| WO | WO9409022 A1 | 4/1994 |
| WO | WO9503428 A1 | 2/1995 |
| WO | WO9708343 A1 | 3/1997 |
| WO | WO9802577 A1 | 1/1998 |
| WO | WO0003034 A2 | 1/2000 |
| WO | 0008507 A2 | 2/2000 |
| WO | WO0020641 A1 | 4/2000 |
| WO | WO0058507 A1 | 10/2000 |
| WO | WO02079771 A1 | 10/2002 |
| WO | 03073149 A1 | 9/2003 |
| WO | WO2005017485 A2 | 2/2005 |
| WO | 2007055302 A1 | 5/2007 |
| WO | 2008133729 A2 | 11/2008 |

OTHER PUBLICATIONS

Search Report and Written Opinion from PCT Application No. PCT/US2007/084786 dated Nov. 28, 2008.

Search Report and Written Opinion from PCT Application No. PCT/US2007/084800 dated May 14, 2008.

Search Report from corresponding EP Application No. 11175116.0-2404 dated Sep. 19, 2011.

Search Report and Written Opinion from PCT Application No. PCT/US2007/084783 dated Dec. 1, 2008.

Search Report from corresponding EP Application No. 11175305.9-2404 dated Oct. 31, 2011.

Rene et al., "Methods of immunological analysis", VCH Verlagsgesellschaft MBH, vol. 3, pp. 318-319, 1993.

Kajtar et al., "Automated Fluorescent in Situ Hybridization (FISH) Analysis of t(9:22)(q34;q11) in Interphase Nuclei", Cytometry A, vol. 69, No. 6, pp. 506-514, Jun. 1, 2006.

Masseyeff et al., "Methods of Immunological Analysis", vol. 3, pp. 318-319, 1993.

Wählby et al., "Sequential Immunofluorescence Staining and Image Analysis for Detection of Large Numbers of Antigens in Individual Cell Nuclei", Cytometry, vol. 47, pp. 32-41, 2002.

Segal et al., "Decomposition of Pinacyanol Chloride Dye Using Several Manganese Oxide Catalysts", Chem. Mater., vol. 9, pp. 2526-2532, 1997.

Mittag et al., "Sequential Photobleaching of Fluorochromes for Polychromatic Slide-Based Cytometry", Cytometry Part A, vol. 69A, pp. 139-141, 2006.

Laffers et al., "Iterative Restaining as a Pivotal Tool for n-Color Immunophenotyping by slide-Based Cytometry", Cytometry, Part A, vol. 69A, pp. 127-130, 2006.

Gharahdaghi et al., "Mass Spectrometric Identification of Proteins From Silver-Stained Polyacrylamide Gel: A Method for the Removal of Silver Ions to Enhance Sensitivity", Electrophoresis, vol. 20, pp. 601-605, 1999.

Press et al., "Amplification and Overexpression of HER-2/neu in Carcinomas of the Salivary Gland: Correlation With Poor Prognosis1", Cancer Research, vol. 54, pp. 5675-5682, Nov. 1, 1994.

Ratcliffe et al., "The Combination of In Situ Hybridization and Immunohistochemical Analysis: An Evaluation of Her2/neu Expression in Paraffin-Embedded Breast Carcinomas and Adjacent Normal-Appearing Breast Epithelium", Modern Pathology, vol. 10, No. 12, pp. 1247-1252, 1997.

Gardiner et al., "Development of a Technique that Allows Simultaneous Assessment of the Morphology and Gene Amplification by FISH: Application to HER-2/Neu Amplification in Breast Cancer", Modern Pathology. vol. 12, No. 1, p. 191A and cover sheet, Jan. 1999, Abstract.

* cited by examiner

SEQUENTIAL ANALYSIS OF BIOLOGICAL SAMPLES

CROSS-REFERENCE TO RELATED APPLICATIONS

This is a Continuation of U.S. patent application Ser. No. 12/611,299, which was filed on Nov. 3, 2009 and entitled SEQUENTIAL ANALYSIS OF BIOLOGICAL SAMPLES which is a Divisional of U.S. patent application Ser. No. 11/560,599, which was filed on Nov. 16, 2006, and entitled SEQUENTIAL ANALYSIS OF BIOLOGICAL SAMPLES, both of which are hereby incorporated by reference in their entirety.

BACKGROUND

Disclosed herein are methods for sequentially analyzing a biological sample to discern characteristics of the sample, for example, the presence, absence, concentration, and/or spatial distribution of multiple biological targets in a biological sample.

Various methods may be used in biology and in medicine to observe different targets in a biological sample. For example, analysis of proteins in histological sections and other cytological preparations may be performed using the techniques of histochemistry, immunohistochemistry (IHC), or immunofluorescence.

Many of the current techniques may detect only a few targets at one time (such as, IHC where number of targets detectable is limited by the florescence-based detection system) in a single sample. Further analysis of targets may require use of additional biological samples from the source limiting the ability to determine relative characteristics of the targets such as the presence, absence, concentration, and/or the spatial distribution of multiple biological targets in the biological sample. Moreover, in certain instances, a limited amount of sample may be available for analysis or the individual sample may require further analysis. Thus, methods, agents, and devices capable of iteratively analyze an individual sample are needed.

BRIEF DESCRIPTION

In some embodiments, methods of detecting multiple targets in a biological sample are provided. The methods include the steps of contacting the sample with a first probe, physically binding the first probe to a first target, observing a first signal from the first probe, applying a chemical agent to modify the first signal, contacting the sample with a second probe, physically binding the second probe to a second target, and observing a second signal from the second probe. The process of contacting, binding, observing and modifying may be iteratively repeated.

In some embodiments, kits for detection of multiple targets in a biological sample are provided. The kit includes a first probe capable of binding to a first target and providing a first signal and a second probe capable of binding to a second target and providing a second signal. The first probe is responsive to a chemical agent to result in modification of the first signal. The kits provided herein may also include additional (e.g., second, third, or $n^{th}$) probes capable of binding to a target and providing multiple signals.

In some embodiments, devices including a sample handling system, a reagent dispensing system, and a signal detection system are provided. The device may be employed to detect multiple targets in a biological sample using the method including the steps of: contacting the sample with a first probe, physically binding the first probe to a first target, observing a first signal from the first probe, applying a chemical agent to modify the first signal, contacting the sample with a second probe, physically binding the second probe to a second target, and observing a second signal from the second probe.

DETAILED DESCRIPTION

Figure 1:
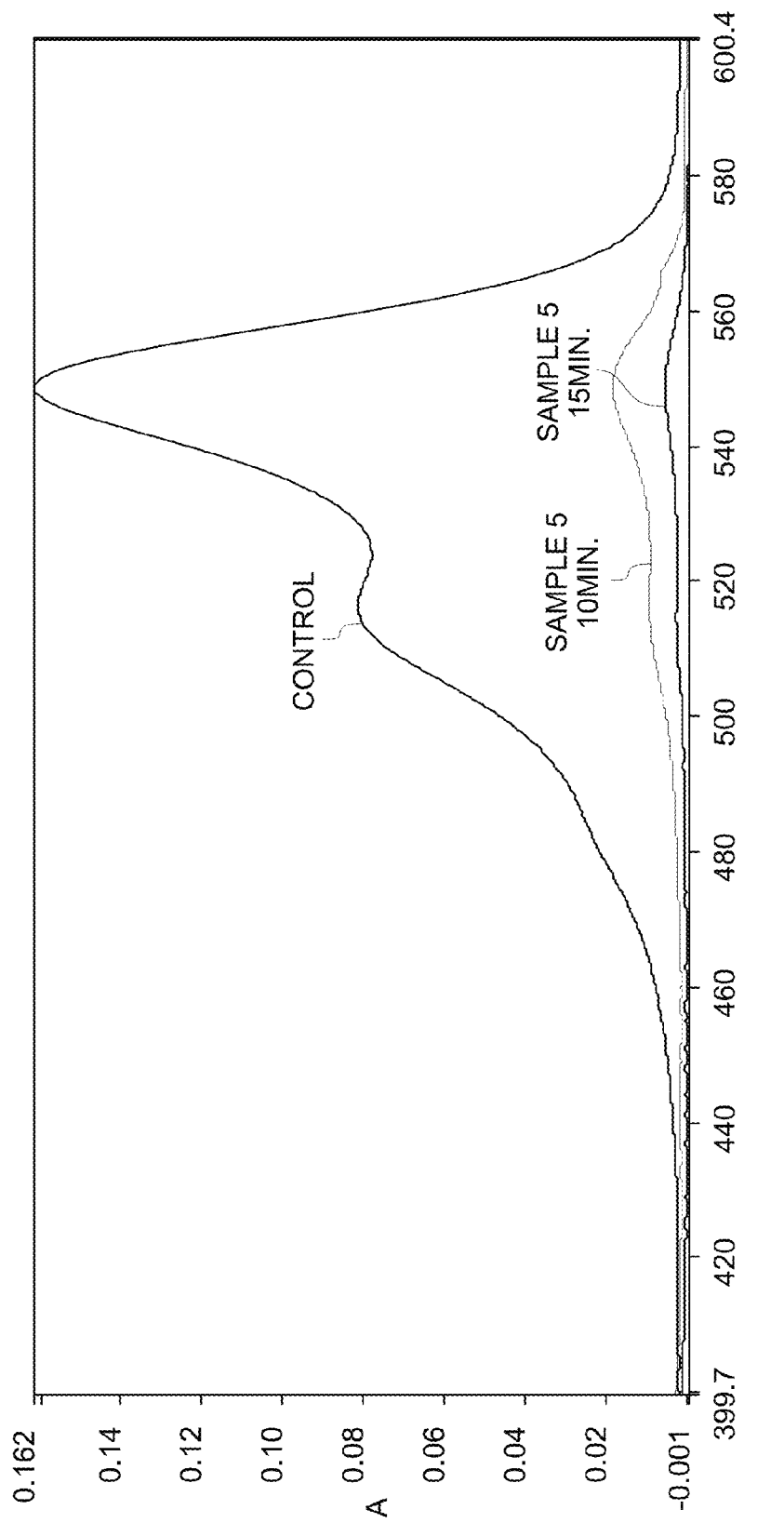
FIG. 1 is the absorbance spectra of Sample 1 as a function of wavelength, after 10 minutes and 15 minutes.

To more clearly and concisely describe and point out the subject matter of the claimed invention, the following definitions are provided for specific terms, which are used in the following description and the appended claims.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

"Biological sample" as used herein, refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine). Biological samples may be dispersed in solution or may be immobilized on a solid support, such as in blots, assays, arrays, glass slides, microtiter, or ELISA plates.

A biological sample may be of prokaryotic origin or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee or human).

"Target," as used herein, generally refers to the component of a biological sample that may be detected when present in the biological sample. The target may be any substance for which there exists a naturally occurring specific binder (e.g., an antibody), or for which a specific binder may be prepared (e.g., a small molecule binder). In general, the binder portion of the probe may bind to target through one or more discrete chemical moieties of the target or a three-dimensional structural component of the target (e.g., 3D structures resulting from peptide folding). The target may include one or more of peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens.

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')$_2$, or Fab'). In addition, aggregates, polymers, and conjugates of immunoglobulins or their fragments may be used where appropriate so long as binding affinity for a particular molecule is substantially maintained.

As used herein, the term "probe" refers to an agent including a binder and a signal generator. In some embodiments, the binder and the signal generator of the probe are embodied in a single entity (e.g., a radioactive or fluorescent molecule capable of binding a target). In alternative embodiments, the binder and the signal generator are embodied in discrete entities (e.g., a primary antibody capable of binding target and labeled secondary antibody capable of binding the primary antibody).

When the binder and signal generator are separate entities they may be applied to a biological sample in a single step or separate steps. Thus, the binder and signal generator may be attached directly (e.g., via a radiolabeled atom incorporated into the binder) or indirectly (e.g., through a linker, which may include a cleavage site) and applied to the biological sample in a single step. For some embodiments in which the binder and the signal generator are separate entities, they may be pre-attached prior to application to the biological sample and applied to the biological sample in a single step. In other embodiments in which the binder and signal generator are separate entities, they may be applied to the biological sample independently and associate following application.

As used herein, the term "binder" refers to a biological molecule that may non-covalently bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, haptens, and the like. A suitable binder may be selected depending on the sample to be analyzed and the targets available for detection. For example, a target in the sample may include a ligand and the binder may include a receptor or a target may include a receptor and the probe may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal, or a radioactive signal. Examples of signal generators useful in the inventive methods include, for example, a chromophore, a fluorophore, a Raman-active tag, a radioactive label, an enzyme, an enzyme substrate, or combinations thereof. As stated above, with regard to the probe, the signal generator and the binder may be present in a single entity (e.g., a target binding protein with a fluorescent label or radiolabel). And, in other embodiments the binder and the signal generator are discrete entities (e.g., target receptor protein and antibody against the that particular receptor protein) that associate with each other prior to or upon introduction to the sample.

As used herein, the term "fluorophore" refers to a chemical compound, which when excited by exposure to a particular wavelength of light, emits light (at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2' disulfonic acid, acridine, derivatives of acridine and acridine isothiocyanate, 5-(2'-aminoethyl)amino naphthalene-1-sulfonic acid (EDANS),4-amino-N-[3-vinylsulfonyl)phenyl] naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, and squaraines.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (KA) for the target no lower than about $10^5$ $M^{-1}$ under ambient conditions (i.e., a pH of about 6 to about 8 and temperature ranging from about 0° C. to about 37° C.).

As used herein, the term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

The invention includes embodiments that relate generally to methods applicable in analytical, diagnostic, or prognostic applications such as analyte detection, histochemistry, immunohistochemistry, or immunofluorescence. In some embodiments, the methods disclosed herein may be particularly applicable in histochemistry, immunohistochemistry, or immunofluorescence.

The disclosed methods relate generally to detection of multiple targets in a single biological sample. In some embodiments, methods of detecting multiple targets in a single biological sample using the same detection channel are disclosed. The targets may be present on the surface of cells in suspension, on the surface of cytology smears, on the surface of histological sections, on the surface of DNA microarrays, on the surface of protein microarrays, or on the surface of solid supports (such as gels, blots, glass slides, beads, or ELISA plates).

The methods disclosed herein may allow detection of a plurality of targets in the same biological sample with little or no effect on the integrity of the biological sample. Detecting the targets in the same biological sample may further provide spatial information about the targets in the biological sample. Methods disclosed herein may also be applicable in analytical applications where a limited amount of biological sample may be available for analysis and the same sample may have to e processed for multiple analyses. Furthermore, the same detection channel may be employed for detection of different targets in the sample, enabling fewer chemistry requirements for analyses of multiple targets. The methods may further facilitate analyses based on detection methods that may be limited in the number of simultaneously detectable targets because of limitations of resolvable signals. For example, using fluorescent-based detection, the number of targets that may be simultaneously detected may be limited to about four as only about four fluorescent signals may be resolvable based on their excitation and emission wavelength properties. In some embodiments, the methods disclosed herein may allow detection of greater than four targets using fluorescent-based detection system.

In some embodiments, the method of detecting multiple targets in a biological sample includes sequential detection of targets in the biological sample. The method generally includes the steps of detecting a first target in the biological sample, modifying the signal from the first target using a chemical agent, and detecting a second target in the biological sample. The method may further include repeating the step of modification of signal from the second target followed by detecting a third target in the biological sample, and so forth.

In some embodiments, the method includes the steps of contacting a biological sample with a first probe and physically binding a first probe to a first target. The method further includes observing a first signal from the first probe. A chemical agent is applied to the probe to modify the first signal. The method further includes contacting the biological sample with a second probe and physically binding the second probe to a second target in the biological sample followed by observing a second signal from the second probe.

Biological Samples

A biological sample in accordance with one embodiment of the invention may be solid or fluid. Suitable examples of biological samples may include, but are not limited to, but are not limited to, cultures, blood, plasma, serum, saliva, cerebral spinal fluid, pleural fluid, milk, lymph, sputum, semen, urine, stool, tears, saliva, needle aspirates, external sections of the skin, respiratory, intestinal, and genitourinary tracts, tumors, organs, cell cultures or cell culture constituents, or solid tissue sections. In some embodiments, the biological sample may be analyzed as is, that is, without harvest and/or isolation of the target of interest. In an alternate embodiment, harvest and isolation of targets may be performed prior to analysis. In some embodiments, the methods disclosed herein may be particularly suitable for in-vitro analysis of biological samples.

A biological sample may include any of the aforementioned samples regardless of their physical condition, such as, but not limited to, being frozen or stained or otherwise treated. In some embodiments, a biological sample may include compounds which are not naturally intermixed with the sample in nature such as preservatives, anticoagulants, buffers, fixatives, nutrients, antibiotics, or the like.

In some embodiments, a biological sample may include a tissue sample, a whole cell, a cell constituent, a cytospin, or a cell smear. In some embodiments, a biological sample essentially includes a tissue sample. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In some embodiments, a biological sample includes tissue sections of colon, normal breast tissue, prostate cancer, colon adenocarcinoma, breast tissue microarray, breast TMA, or normal prostate. A tissue section may include a single part or piece of a tissue sample, for example, a thin slice of tissue or cells cut from a tissue sample. In some embodiments, multiple sections of tissue samples may be taken and subjected to analysis, provided the methods disclosed herein may be used for analysis of the same section of the tissue sample with respect to at least two different targets (at morphological or molecular level). In some embodiments, the same section of tissue sample may be analyzed with respect to at least four different targets (at morphological or molecular level). In some embodiments, the same section of tissue sample may be analyzed with respect to greater than four different targets (at morphological or molecular level). In some embodiments, the same section of tissue sample may be analyzed at both morphological and molecular levels. A tissue section, if employed as a biological sample may have a thickness in a range that is less than about 100 micrometers, in a range that is less than about 50 micrometers, in a range that is less than about 25 micrometers, or in range that is less than about 10 micrometers.

Targets

A target according to an embodiment of the invention may be present on the surface of a biological sample (for example, an antigen on a surface of a tissue section) or present in the bulk of the sample (for example, an antibody in a buffer solution). In some embodiments, a target may not be inherently present on the surface of a biological sample and the biological sample may have to be processed to make the target available on the surface. In some embodiments, the target may be soluble in a body fluid such as blood, blood plasma, serum, or urine. In some embodiments, the target may be in a tissue, either on a cell surface, or within a cell.

Suitability of target(s) to be analyzed may be determined by the type and nature of analysis required for the biological sample. In some embodiments, a target may provide information about the presence or absence of an analyte in the biological sample. In another embodiment, a target may provide information on a state of a biological sample. For example, if the biological sample includes a tissue sample, the methods disclosed herein may be used to detect target(s) that may help in comparing different types of cells or tissues, comparing different developmental stages, detecting the presence of a disease or abnormality, or determining the type of disease or abnormality.

Suitable targets may include one or more of peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. One or more of the aforementioned targets may be characteristic of particular cells, while other targets may be associated with a particular disease or condition. In some embodiments, targets in a tissue sample that may be detected and analyzed using the methods disclosed herein may include, but are not limited to, but are not limited to, prognostic targets, hormone or hormone receptor targets, lymphoid targets, tumor targets, cell cycle associated targets, neural tissue and tumor targets, or cluster differentiation targets Suitable examples of prognostic targets may include enzymatic targets such as galactosyl transferase II, neuron specific enolase, proton ATPase-2, or acid phosphatase.

Suitable examples of hormone or hormone receptor targets may include human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, or insulin receptor.

Suitable examples of lymphoid targets may include alpha-1-antichymotrypsin, alpha-1-antitrypsin, B cell target, bcl-2, bcl-6, B lymphocyte antigen 36 kD, BM1 (myeloid target), BM2 (myeloid target), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage target, muramidase (lysozyme), p80 anaplastic lymphoma kinase, plasma cell target, secretory leukocyte protease inhibitor, T cell antigen receptor (JOVI 1), T cell antigen receptor (JOVI 3), terminal deoxynucleotidyl transferase, or unclustered B cell target.

Suitable examples of tumour targets may include alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, gross cystic disease fluid protein-15, hepatocyte specific antigen, heregulin, human gastric mucin, human milk fat globule, MAGE-1, matrix metalloproteinases, melan A, melanoma target (HMB45), mesothelin, metallothionein, microphthalmia transcription factor (MITF), Muc-1 core glycoprotein. Muc-1 glycoprotein, Muc-2 glycoprotein, Muc-5AC glycoprotein, Muc-6 glycoprotein, myeloperoxidase, Myf-3 (Rhabdomyosarcoma target), Myf-4 (Rhabdomyosarcoma target), MyoD1 (Rhabdomyosarcoma target), myoglobin, nm23 protein, placental alkaline phosphatase, prealbumin, prostate specific antigen, prostatic acid phosphatase, prostatic inhibin peptide, PTEN, renal cell carcinoma target, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, or von Willebrand factor.

Suitable examples of cell cycle associated targets may include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mcl-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, or topoisomerase II beta.

Suitable examples of neural tissue and tumor targets may include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma target, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, or ubiquitin.

Suitable examples of cluster differentiation targets may include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, and TCR-zeta.

Other suitable prognostic targets hormone or hormone receptor targets lymphoid targets tumor targets cell cycle associated targets neural tissue and tumor targets include centromere protein-F (CENP-F), giantin, involucrin, lamin A&C(XB 10), LAP-70, mucin, nuclear pore complex proteins, p180 lamellar body protein, ran, cathepsin D, Ps2 protein, Her2-neu, P53, S100, epithelial target antigen (EMA), TdT, MB2, MB3, PCNA, or Ki67.

Probes

In some embodiments, the present methods may employ probes that do not include an intrinsic signal generator. In some alternative embodiments, the probe does include a binder capable of binding to the target and a signal generator capable of providing a detectable signal. Thus, In some embodiments, the binder and the signal generator are not be associated to each other and may be present as a mixture or as separate components that associate following sequential application of the binder and signal generator to the biological sample. In alternate embodiments, the binder and the signal generator may be associated to each other. As used herein, "associated" generally refers to two entities (for example, binder and signal generator) stably bound to one another by any physicochemical means. The nature of the association may be such that it does not substantially impair the effectiveness of either entity. A binder and a signal generator may be associated to each other through covalent or non-covalent interactions. Non-covalent interactions may include, but are not limited to, hydrophobic interactions, ionic interactions, hydrogen-bond interactions, high affinity interactions (such as, biotin-avidin or biotin-streptavidin complexation), or other affinity interactions.

In some embodiments, a binder and a signal generator may be associated to each other directly (that is without any linkers). In other embodiments, a binder and a signal generator may be conjugated to each other via a linker. A linker may include a form of linking structure or sequence formed due to the non-covalent or covalent bond formation. In some embodiments, the linker may be chemically stable, that is, may maintain its integrity in the presence of a chemical agent. In some embodiments, the linker may be susceptible to chemical agents that is may be capable of dissociating, cleaving, or hydrolyzing in the presence of a chemical agent. Suitable examples of linkers may include disulfide bonds (e.g., SPDP or SMPT), pH sensitive structures/sequences, structures/sequences that may be reduced in the presence of an reducing agent, structures/sequences that may be oxidized in the presence of an oxidizing agent, or any other chemical or physical bond that may be easily manipulated (dissociated, cleaved, or hydrolyzed) in the presence of a chemical agent.

In some embodiments, the binder may be intrinsically labeled with a signal generator (for example, if the binder is a protein, during synthesis using a detectably labeled amino acid). A binder that is intrinsically labeled may not require a separate signal generator in order to be detected. Rather the intrinsic label may be sufficient for rendering the probe detectable. In alternate embodiments, the binder may be labeled by binding to it a specific signal generator (i.e., extrinsically labeled).

A binder and a signal generator may be chemically linked to each other through functional groups capable of reacting and forming a linkage under suitable conditions. Suitable examples of functional group combinations may include, but are not limited to, amine ester and amines or anilines; acyl azide and amines or anilines; acyl halides and amines, anilines, alcohols, or phenols; acyl nitrile and alcohols or phenols; aldehyde and amines or anilines; alkyl halide and amines, anilines, alcohols, phenols or thiols; alkyl sulfonate and thiols, alcohols or phenols; anhydride and alcohols, phenols, amines or anilines; aryl halide and thiols; aziridine and thiols or thioethers; carboxylic acid and amines, anilines, alcohols or alkyl halides; diazoalkane and carboxylic acids; epoxide and thiols; haloacetamide and thiols; halotriazin and amines, anilines or phenols; hydrazine and aldehydes or ketones; hydroxyamine and aldehydes or ketones; imido ester and amines or anilines; isocyanate and amines or anilines; and isothiocyanate and amines or anilines. A functional group in one of the aforementioned functional group pair may be present in a binder and a corresponding functional group may be present in the signal generator. For example, a binder may include a carboxylic acid and the signal generator may include an amine, aniline, alcohol or acyl halide, or vice versa. Conjugation between the binder and the signal generator may be effected in this case by formation of an amide or an ester linkage.

Binders

The methods disclosed herein involve the use of binders that physically bind to the target in a specific manner. In some embodiments, a binder may bind to a target with sufficient specificity, that is, a binder may bind to a target with greater affinity than it does to any other molecule. In some embodiments, the binder may bind to other molecules, but the binding may be such that the non-specific binding may be at or near background levels. In some embodiments, the affinity of the binder for the target of interest may be in a range that is at least 2-fold, at least 5-fold, at least 10-fold, or more than its affinity for other molecules. In some embodiments, binders with the greatest differential affinity may be employed, although they may not be those with the greatest affinity for the target.

Binding between the target and the binder may be affected by physical binding. Physical binding may include binding effected using non-covalent interactions. Non-covalent interactions may include, but are not limited to, interactions, ionic interactions, hydrogen-bond interactions, or affinity interactions (such as, biotin-avidin or biotin-streptavidin complexation). In some embodiments, the target and the binder may have areas on their surfaces or in cavities giving rise to specific recognition between the two resulting in physical binding. In some embodiments, a binder may bind to a biological target based on the reciprocal fit of a portion of their molecular shapes.

Binders and their corresponding targets may be considered as binding pairs, of which non-limiting examples include immune-type binding-pairs, such as, antigen/antibody, antigen/antibody fragment, or hapten/anti-hapten; nonimmune-type binding-pairs, such as biotin/avidin, biotin/streptavidin, folic acid/folate binding protein, hormone/hormone receptor, lectin/specific carbohydrate, enzyme/enzyme, enzyme/substrate, enzyme/substrate analog, enzyme/pseudo-substrate (substrate analogs that cannot be catalyzed by the enzymatic activity), enzyme/co-factor, enzyme/modulator, enzyme/inhibitor, or vitamin B12/intrinsic factor. Other suitable examples of binding pairs may include complementary nucleic acid fragments (including DNA sequences, RNA sequences, PNA sequences, and peptide nucleic acid sequences); Protein A/antibody; Protein G/antibody; nucleic acid/nucleic acid binding protein; or polynucleotide/polynucleotide binding protein.

In some embodiments, the binder may be a sequence- or structure-specific binder, wherein the sequence or structure of a target recognized and bound by the binder may be sufficiently unique to that target.

In some embodiments, the binder may be structure-specific and may recognize a primary, secondary, or tertiary structure of a target. A primary structure of a target may include specification of its atomic composition and the chemical bonds connecting those atoms (including stereochemistry), for example, the type and nature of linear arrangement of amino acids in a protein. A secondary structure of a target may refer to the general three-dimensional form of segments of biomolecules, for example, for a protein a secondary structure may refer to the folding of the peptide "backbone" chain into various conformations that may result in distant amino acids being brought into proximity with each other. Suitable examples of secondary structures may include, but are not limited to, alpha helices, beta pleated sheets, or random coils. A tertiary structure of a target may be is its overall three dimensional structure. A quaternary structure of a target may be the structure formed by its noncovalent interaction with one or more other targets or macromolecules (such as protein interactions). An example of a quaternary structure may be the structure formed by the four-globin protein subunits to make hemoglobin. A binder in accordance with the embodiments of the invention may be specific for any of the aforementioned structures.

An example of a structure-specific binder may include a protein-specific molecule that may bind to a protein target. Examples of suitable protein-specific molecules may include antibodies and antibody fragments, nucleic acids (for example, aptamers that recognize protein targets), or protein substrates (non-catalyzable).

In some embodiments, a target may include an antigen and a binder may include an antibody. A suitable antibody may include monoclonal antibodies, polyclonal antibodies, multispecific antibodies (for example, bispecific antibodies), or antibody fragments so long as they bind specifically to a target antigen.

In some embodiments, a target may include a monoclonal antibody. A "monoclonal antibody" may refer to an antibody obtained from a population of substantially homogeneous antibodies, that is, the individual antibodies comprising the population are identical except for possible naturally occurring mutations that may be present in minor amounts. Monoclonal antibodies may be highly specific, being directed against a single antigenic site. Furthermore, in contrast to (polyclonal) antibody preparations that typically include different antibodies directed against different determinants (epitopes), each monoclonal antibody may be directed against a single determinant on the antigen. A monoclonal antibody may be prepared by any known method such as the hybridoma method, by recombinant DNA methods, or may be isolated from phage antibody libraries.

In some embodiments, a biological sample may include a cell or a tissue sample and the methods disclosed herein may be employed in immunohistochemistry (IHC) Immunochemistry may involve binding of a target antigen to an antibody-based binder to provide information about the tissues or cells (for example, diseased versus normal cells). Examples of antibodies (and the corresponding diseases/disease cells)

suitable as binders for methods disclosed herein include, but are not limited to, anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multi-drug resistance), anti-CEA antibody (carcinoembryonic antigen), anti-retinoblastoma protein (Rb) antibody, anti-ras oneoprotein (p21) antibody, anti-Lewis X (also called CD15) antibody, anti -Ki-67 antibody (cellular proliferation), anti-PCNA (multiple cancers) antibody, anti-CD 3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblasic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD 22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD 41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salvary, glial cells), anti-tau antigen antibody (amyloid associated disease), anti-fibrin antibody (epithelial cells), anti-keratins antibody, anti-cytokeratin antibody (tumor), anti-alpha-catenin (cell membrane), or anti-Tn-antigen antibody (colon carcinoma, adenocarcinomas, and pancreatic cancer).

Other specific examples of suitable antibodies may include, but are not limited to, but are not limited to, anti proliferating cell nuclear antigen, clone pc10 (Sigma Aldrich, P8825); anti smooth muscle alpha actin (5 mA), clone 1A4 (Sigma, A2547); rabbit anti beta catenin (Sigma, C 2206); mouse anti pan cytokeratin, clone PCK-26 (Sigma, C1801); mouse anti estrogen receptor alpha, clone 1D5 (DAKO, M 7047); beta catenin antibody, clone 15B8 (Sigma, C 7738); goat anti vimentin (Sigma, V4630); cycle androgen receptor clone AR441 (DAKO, M3562); Von Willebrand Factor 7, keratin 5, keratin 8/18, e-cadherin, Her2/neu, Estrogen receptor, p53, progesterone receptor, beta catenin; donkey anti-mouse (Jackson Immunoresearch, 715-166-150); or donkey anti rabbit (Jackson Immunoresearch, 711-166-152).

In some embodiments, a binder may be sequence-specific. A sequence-specific binder may include a nucleic acid and the binder may be capable of recognizing a particular linear arrangement of nucleotides or derivatives thereof in the target. In some embodiments, the linear arrangement may include contiguous nucleotides or derivatives thereof that may each bind to a corresponding complementary nucleotide in the binder. In an alternate embodiment, the sequence may not be contiguous as there may be one, two, or more nucleotides that may not have corresponding complementary residues on the probe. Suitable examples of nucleic acid-based binders may include, but are not limited to, DNA or RNA oligonucleotides or polynucleotides. In some embodiments, suitable nucleic acids may include nucleic acid analogs, such as dioxygenin dCTP, biotin dcTP 7-azaguanosine, azidothymidine, inosine, or uridine.

In certain embodiments, both the binder and the target may include nucleic acids. In some embodiments, a nucleic-acid based binder may form a Watson-Crick bond with the nucleic acid target. In another embodiment, the nucleic acid binder may form a Hoogsteen bond with the nucleic acid target, thereby forming a triplex. A nucleic acid binder that binds by Hoogsteen binding may enter the major groove of a nucleic acid target and hybridizes with the bases located there. Suitable examples of the above binders may include molecules that recognize and bind to the minor and major grooves of nucleic acids (for example, some forms of antibiotics.) In certain embodiments, the nucleic acid binders may form both Watson-Crick and Hoogsteen bonds with the nucleic acid target (for example, bis PNA probes are capable of both Watson-Crick and Hoogsteen binding to a nucleic acid).

The length of nucleic acid binder may also determine the specificity of binding. The energetic cost of a single mismatch between the binder and the nucleic acid target may be relatively higher for shorter sequences than for longer ones. In some embodiments, hybridization of smaller nucleic acid binders may be more specific than the hybridization of longer nucleic acid probes, as the longer probes may be more amenable to mismatches and may continue to bind to the nucleic acid depending on the conditions. In certain embodiments, shorter binders may exhibit lower binding stability at a given temperature and salt concentration. Binders that may exhibit greater stability to bind short sequences may be employed in this case (for examples, bis PNA). In some embodiments, the nucleic acid binder may have a length in range of from about 4 nucleotides to about 12 nucleotides, from about 12 nucleotides to about 25 nucleotides, from about 25 nucleotides to about 50 nucleotides, from about 50 nucleotides to about 100 nucleotides, from about 100 nucleotides to about 250 nucleotides, from about 250 nucleotides to about 500 nucleotides, or from about 500 nucleotides to about 1000 nucleotides. In some embodiments, the nucleic acid binder may have a length in a range that is greater than about 1000 nucleotides. Notwithstanding the length of the nucleic acid binder, all the nucleotide residues of the binder may not hybridize to complementary nucleotides in the nucleic acid target. For example, the binder may include 50 nucleotide residues in length, and only 25 of those nucleotide residues may hybridize to the nucleic acid target. In some embodiments, the nucleotide residues that may hybridize may be contiguous with each other. The nucleic acid binders may be single stranded or may include a secondary structure. In some embodiments, a biological sample may include a cell or a tissue sample and the biological sample may be subjected to in-situ hybridization (ISH) using a nucleic acid binder. In some embodiments, a tissue sample may be subjected to in-situ hybridization in addition to immunohistochemistry (IHC) to obtain desired information regarding the tissue sample.

Regardless of the type of binder and the target, the specificity of binding between the binder and the target may also be affected depending on the binding conditions (for example, hybridization conditions in case of complementary nucleic acids. Suitable binding conditions may be realized by modulation one or more of pH, temperature, or salt concentration.

As noted hereinabove, a binder may be intrinsically labeled (signal generator attached during synthesis of binder) with a signal generator or extrinsically labeled (signal generator attached during a later step). For example for a protein-based binder, an intrinsically labeled binder may be prepared by employing labeled amino acids. Similarly, an intrinsically labeled nucleic acid may be synthesized using methods that incorporate signal generator-labeled nucleotides directly into the growing nucleic acid. In some embodiments, a binder may be synthesized in a manner such that signal generators may e incorporated at a later stage. For example, this latter labeling may be accomplished by chemical means by the introduction of active amino or thiol groups into nucleic acids of peptide chains. In some embodiments, a binder such a protein (for example, an antibody) or a nucleic acid (for example, a DNA) may be directly chemically labeled using appropriate chemistries for the same.

In some embodiments, combinations of binders may be used that may provide greater specificity or in certain embodiments amplification of the signal. Thus, In some embodiments, a sandwich of binders may be used, where the first binder may bind to the target and serve to provide for secondary binding, where the secondary binder may or may not include a signal generator, which may further provide for tertiary binding (if required) where the tertiary binding member may include a signal generator.

Suitable examples of binder combinations may include primary antibody-secondary antibody, complementary nucleic acids, or other ligand-receptor pairs (such as biotin-streptavidin). Some specific examples of suitable binder pairs may include mouse anti-myc for recombinant expressed proteins with c-myc epitope; mouse anti-H isG for recombinant protein with His-Tag epitope, mouse anti-xpress for recombinant protein with epitope-tag, rabbit anti-goat for goat IgG primary molecules, complementary nucleic acid sequence for a nucleic acid; mouse anti-thio for thioredoxin fusion proteins, rabbit anti-GFP for fusion protein, jacalin for α-D-galactose; and melibiose for carbohydrate-binding proteins, sugars, nickel couple matrix or heparin.

In some embodiments, a combination of a primary antibody and a secondary antibody may be used as a binder. A primary antibody may be capable of binding to a specific region of the target and the secondary antibody may be capable of binding to the primary antibody. A secondary antibody may be attached to a signal generator before binding to the primary antibody or may be capable of binding to a signal generator at a later step. In an alternate embodiment, a primary antibody and specific binding ligand-receptor pairs (such as biotin-streptavidin) may be used. The primary antibody may be attached to one member of the pair (for example biotin) and the other member (for example streptavidin) may be labeled with a signal generator. The secondary antibody, avidin, streptavidin, or biotin may be each independently labeled with a signal generator.

In some embodiments, the methods disclosed herein may be employed in an immunohistochemical procedure, and a primary antibody may be used to specifically bind the target antigen in the tissue sample. A secondary antibody may be used to specifically bind to the primary antibody, thereby forming a bridge between the primary antibody and a subsequent reagent (for example a signal generator), if any. For example, a primary antibody may be mouse IgG (an antibody created in mouse) and the corresponding secondary antibody may be goat anti-mouse (antibody created in goat) having regions capable of binding to a region in mouse IgG.

In some embodiments, signal amplification may be obtained when several secondary antibodies may bind to epitopes on the primary antibody. In an immunohistochemical procedure a primary antibody may be the first antibody used in the procedure and the secondary antibody may be the second antibody used in the procedure. In some embodiments, a primary antibody may be the only antibody used in an IHC procedure.

Signal Generators

The type of signal generator suitable for the methods disclosed herein may depend on a variety of factors, including the nature of the analysis being conducted, the type of the energy source and detector used, the type of chemical agent employed, the type of binder, the type of target, or the mode of attachment between the binder and the signal generator (e.g., cleavable or non-cleavable).

A suitable signal generator may include a molecule or a compound capable of providing a detectable signal. A signal generator may provide a characteristic signal following interaction with an energy source or a current. An energy source may include electromagnetic radiation source and a fluorescence excitation source. Electromagnetic radiation source may be capable of providing electromagnetic energy of any wavelength including visible, infrared, and ultraviolet. Electromagnetic radiation may be in the form of a direct light source or may be emitted by a light emissive compound such as a donor fluorophore. A fluorescence excitation source may be capable of making a source fluoresce or may give rise to photonic emissions (that is, electromagnetic radiation, directed electric field, temperature, physical contact, or mechanical disruption). Suitable signal generators may provide a signal capable of being detected by a variety of methods including optical measurements (for example, fluorescence), electrical conductivity, or radioactivity. Suitable signal generators may be, for example, light emitting, energy accepting, fluorescing, radioactive, or quenching.

A suitable signal generator may be sterically and chemically compatible with the constituents to which it is bound, for example, a binder. Additionally, a suitable signal generator may not interfere with the binding of the binder to the target, nor may it affect the binding specificity of the binder. A suitable signal generator may be organic or inorganic in nature. In some embodiments, a signal generator may be of a chemical, peptide or nucleic acid nature.

A signal generator may be directly or indirectly detectable. A directly detectable moiety may be one that may be detected directly by its ability to emit a signal, such as for example a fluorescent label that emits light of a particular wavelength following excitation by light of another lower, characteristic wavelength and/or absorb light of a particular wavelength. An indirectly detectable signal generator may be one that may be detected indirectly by its ability to bind, recruit, and, in some cases, cleave another moiety, which may in turn emit a signal. An example of an indirectly detectable signal generator may be an enzyme-based signal generator, which when contacted with a suitable substrate may cleave the substrate to provide a detectable signal. Alternatively, an indirectly detectable signal generator may be capable of binding a compound that does emit a signal. For example, a signal generator, such as, biotin which itself does not emit a signal when bound to labeled avidin or streptavidin molecules may be detected. Other examples of indirectly detectable signal generators may include ligands that bind specifically to particular receptors. Detectably labeled receptors may be allowed to bind to ligand labeled binders in order to detect the binders. For example, an antibody-based binder may be attached a small hapten and a signal generator may be attached to an anti-hapten antibody that may bind specifically to hapten.

A signal-generator, suitable in accordance with the methods disclosed herein may be amenable to manipulation on application of a chemical agent. In some embodiments, a signal generator may be capable of being chemically destroyed on exposure to a chemical agent. Chemical destruction may include complete disintegration of the signal generator or modification of the signal-generating component of the signal generator. Modification of the signal-generating component may include any chemical modification (such as addition, substitution, or removal) that may result in the modification of the signal generating properties. For example, unconjugating a conjugated signal generator may result in destruction of chromogenic properties of the signal generator. Similarly, substitution of a fluorescence-inhibiting functional group on a fluorescent signal generator may result in modification of its fluorescent properties.

In some embodiments, a signal generator may be associated with the binder via a cleavable linker. A cleavable linker may be susceptible to a chemical agent and may dissociate, hydrolyze, or cleave when contacted with the chemical agent. Cleavage of the cleavable linker may result in removal of the signal generator from the binder and subsequently the biological sample being analyzed. Suitability of a particular signal generator may be determined in part by the chemistry of the signal generator, for example, if a signal generator is amenable to destruction on application of a chemical agent then a cleavable linkage between the signal generator and the binder may not be required. Similarly, if the signal generator is not amenable to chemical destruction, a cleavable linker may be used to remove the signal generator from biological sample. Suitable examples of signal generators are described herein below.

In some embodiments, a signal generator may be selected from a light emissive molecule, a radioisotope (e.g., $P^{32}$ or $H^3$, $^{14}C$, $^{125}I$ and $^{131}I$), an optical or electron density marker, a Raman-active tag an enzyme, an enzyme substrate (for example, a chromogenic substrate), an electron spin resonance molecule (such as for example nitroxyl radicals), an electrical charge transferring molecule (i.e., an electrical charge transducing molecule), a semiconductor nanocrystal, a semiconductor nanoparticle, a colloid gold nanocrystal, a microbead, a magnetic bead, a paramagnetic particle, a quantum dot, or an affinity molecule (e.g., a biotin molecule, a streptavidin molecule, a protein, a peptide, nucleic acid, a carbohydrate, an antigen, a hapten, an antibody, an antibody fragment, or a lipid).

In some embodiments, a signal generator may include a light-emissive molecule. A light emissive molecule may emit light in response to irradiation with light of a particular wavelength. Light emissive molecules may be capable of absorbing and emitting light through luminescence (non-thermal emission of electromagnetic radiation by a material upon excitation), phosphorescence (delayed luminescence as a result of the absorption of radiation), chemiluminescence (luminescence due to a chemical reaction), fluorescence, or polarized fluorescence.

In some embodiments, a signal-generator may be directly detectable. In some embodiments, a signal generator may include a chromophore. In some embodiments, a signal-generator may include a fluorescent molecule or a fluorophore. Suitable chromophores and fluorophores may include one or more molecules listed hereinabove. In some embodiments, the signal generator may be part of a FRET pair. FRET pair includes two fluorophores that are capable of undergoing FRET to produce or eliminate a detectable signal when positioned in proximity to one another. Some examples of donors may include Alexa 488, Alexa 546, BODIPY 493, Oyster 556, Fluor (FAM), Cy3, or TTR (Tamra). Some examples of acceptors may include Cy5, Alexa 594, Alexa 647, or Oyster 656.

In some embodiments, a signal generator may essentially include a fluorophore. In some embodiments, a signal generator may essentially include a fluorophore that may be attached to an antibody, for example, in an immunohistochemistry analysis. Suitable fluorophores that may be conjugated to a primary antibody include, but are not limited to, Fluorescein, Rhodamine, Texas Red, Cy2, Cy3, Cy5, VECTOR Red, ELF™ (Enzyme-Labeled Fluorescence), Cy2, Cy3, Cy3.5, Cy5, Cy7, Fluor X, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY, boron dip yrromethene difluoride, Oregon Green, MITOTRACKER, Red, DiOC.sub.7 (3), DiIC.sub.18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (1R) Dyes, Cyclic GDP-Ribose (cGDPR), Calcofluor White, Lissamine, Umbelliferone, Tyrosine or Tryptophan. In some embodiments, a signal generator may essentially include a cyanine dye. In some embodiments, a signal generator may essentially include one or more cyanine dye (e.g., Cy3 dye, a Cy5 dye, or a Cy7 dye).

In some embodiments, a signal generator may be indirectly detectable, for example, an enzyme/enzyme substrate combination. In some embodiments, an enzyme may precipitate a soluble substrate to form an insoluble product (for example, in immunohistochemistry). Further, an enzyme may catalyze a chemical reaction of a chromogenic substrate that may be measured using a suitable technique. For example, the enzyme may catalyze a color change in a substrate, which can be measured spectrophotometrically. Alternatively, an enzyme may alter the fluorescence or chemiluminescence properties of the substrate. In some embodiments, where enzyme/enzyme substrates may be employed as signal generators, the enzyme-catalyzed reaction product of the substrate may be susceptible to the chemical agent resulting in modification of the product (for example, color destruction using hydrogen peroxide). Suitable examples of enzyme-substrate combinations are described herein below.

Horseradish peroxidase (HRPO) with hydrogen peroxidase as a substrate, wherein the hydrogen peroxidase may oxidize a dye precursor (e.g., orthophenylene diamine (OPD) or 3,3',5,5'-tetramethyl benzidine hydrochloride (TMB)). Other suitable HRPO substrates may include, but are not limited to, but are not limited to, 2,2' Azino-di-3-ethylbenzthiazoline sulfonate (ABTS, green, water soluble), aminoethyl carbazole, 3-amino, 9-ethylcarbazole AEC (3A9EC, red), Alpha-naphthol pyronin (red), 4-chloro-1-naphthol (4C1N, blue, blue-black), 3,3'-diaminobenzidine tetrahydrochloride (DAB, brown), ortho-dianisidine (green), o-phenylene diamine (OPD, brown, water soluble), TACS Blue (blue), TACS Red (red), 3,3',5,5'Tetramethylbenzidine (TMB, green or green/blue), TRUE BLUE (blue), VECTOR VIP (purple), VECTORSG (smoky blue-gray), and Zymed Blue HRP substrate (vivid blue).

Alkaline phosphatase (AP) with para-Nitrophenyl phosphate may be used as a chromogenic substrate. Other suitable AP substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR Black (black), VECTOR, Blue (blue), VECTOR. Red (red), Vega Red (raspberry red color), D-galactosidase ((3-D-Gal) with a chromogenic substrate (e.g., p-nitrophenyl-β-D-galactosidase) or fluorogenic substrate (e.g., 4-methylumbelliferyl-β-D-galactosidase). Other suitable β-galactosidase substrates, include, but are not limited to, 5-bromo-4-chloro-3-indoyl beta-D-galactopyranoside (X-gal, blue precipitate).

Suitable glucose oxidase (GO) substrates, include, but are not limited to, nitroblue tetrazolium (NBT, purple precipitate), tetranitroblue tetrazolium (TNBT, black precipitate), 2-(4-iodophenyl)-5-(4-nitorphenyl) -3-phenyltetrazolium chloride (INT, red or orange precipitate), Tetrazolium blue (blue), Nitrotetrazolium violet (violet), and 3-(4,5-dimethylthiazol-2-yl)-2,5-diphenyltetrazolium bromide (MTT, purple). Tetrazolium substrates may require glucose as a co-substrate. The precipitates associated with each of the substrates listed hereinabove may have unique detectable spectral signatures.

As described hereinabove, one or more of the aforementioned molecules may be used as a signal generator. In some embodiments, one or more of the aforementioned signal generators may not be amenable to chemical destruction and a cleavable linker may be employed to associate the signal generator and the binder. In some embodiments, one or more of the aforementioned signal generators may be amenable to signal destruction and the signal generator may essentially include a molecule capable of being destroyed chemically. In some embodiments, a signal generator may essentially include a fluorophore capable of being destroyed chemically. In some embodiments, a signal generator may essentially include a cyanine dye capable of being destroyed chemically. In some embodiments, a signal generator may essentially include one or more a Cy3 dye, a Cy5 dye, or a Cy7 dye capable of being destroyed or quenched chemically.

Chemical Agents

A chemical agent may include one or chemicals capable of modifying the signal generator or the cleavable linker (if present) between the signal generator and the binder. A chemical agent may be contacted with the signal generator in the form of a solid, a solution, a gel, or a suspension. Suitable chemical agents useful to modify the signal include agents that modify pH (for example, acids or bases), electron donors (e.g., nucleophiles), electron acceptors (e.g., electrophiles), oxidizing agents, reducing agents, or combinations thereof.

In some embodiments, a chemical agent may include a base, for example, sodium hydroxide, ammonium hydroxide, potassium carbonate, or sodium acetate. In some embodiments, a chemical agent may include an acid, for example, hydrochloric acid, sulfuric acid, acetic acid, formic acid, trifluoroacetic acid, or dichloroacetic acid. In some embodiments, a chemical agent may include nucleophiles, for example, cyanides, phosphines, or thiols. In some embodiments, a chemical gent may include reducing agents, for example, phosphines, thiols, sodium dithionite, or hydrides that can be used in the presence of water such as borohydride or cyanoborohydrides. In some embodiments, a chemical agent may include oxidizing agents, for example, active oxygen species, hydroxyl radicals, singlet oxygen, hydrogen peroxide, or ozone. In some embodiments, a chemical agent may include a fluoride, for example tetrabutylammonium fluoride, pyridine-HF, or $SiF_4$.

One or more of the aforementioned chemical agents may be used in the methods disclosed herein depending upon the susceptibility of the signal generator, of the binder, of the target, or of the biological sample to the chemical agent. In some embodiments, a chemical agent that essentially does not affect the integrity of the binder, the target, and the biological sample may be employed. In some embodiments, a chemical agent that does not affect the specificity of binding between the binder and the target may be employed.

In some embodiments, where two or more (up to four) signal generators may be employed simultaneously, a chemical agent may be capable of selectively modifying one or more signal generators. Susceptibility of different signal generators to a chemical agent may depend, in part, to the concentration of the signal generator, temperature, or pH. For example, two different fluorophores may have different susceptibility to a base depending upon the concentration of the base.

Sequentially Analyzing a Biological Sample, Contacting and Binding the Probe

A biological sample may be contacted with a probe to physically bind the probe to a target in the biological sample. In some embodiments, a target may not be easily accessible for binding the probe and a biological sample may be further processed to facilitate the binding between the target and the binder (in the probe). In some embodiments, a probe may be contacted with the biological sample in the form of a solution. Depending on the nature of the binder, the target, and the binding between the two, sufficient contact time may be allowed. In some embodiments, an excess of binder molecules may be employed to ensure all the targets in the biological sample are bound. After a sufficient time has been providing for the binding action, the sample may be contacted with a wash solution (for example an appropriate buffer solution) to wash away any unbound probes. Depending on the concentration and type of probes used, a biological sample may be subjected to a number of washing steps with the same or different washing solutions being employed in each step.

In some embodiments, the biological sample may be contacted with more than one probe in the first contacting step. The plurality of probes may be capable of binding different targets in the biological sample. For example, a biological sample may include two targets: target1 and target2 and two sets of probes may be used in this instance: probe1 (having binder1 capable of binding to target1) and probe2 (having binder2 capable of binding to target2). A plurality of probes may be contacted with the biological sample simultaneously (for example, as a single mixture) or sequentially (for example, a probe1 may be contacted with the biological sample, followed by washing step to remove any unbound probe1, followed by contacting a probe2 with the biological sample, and so forth).

The number of probes that may be simultaneously bound to the target may depend on the type of detection employed, that is, the spectral resolution achievable. For example, for fluorescence-based signal generators, at most four different probes (providing four spectrally resolvable fluorescent signals) may be employed in accordance with the methods disclosed herein. Spectrally resolvable, in reference to a plurality of fluorescent signal generators, implies that the fluorescent emission bands of the signal generators are sufficiently distinct, that is, sufficiently non-overlapping, such that, binders to which the respective signal generators are attached may be distinguished on the basis of the fluorescent signal generated by the respective signal generators using standard photodetection systems. In some embodiments, a biological sample may be essentially contacted with four or less than four probes in the first contacting step.

In some embodiments, a biological sample may include a whole cell, a tissue sample or a microarray. In some embodiments, a biological sample may include a tissue sample. The tissue sample may be obtained by a variety of procedures including, but not limited to surgical excision, aspiration or biopsy. The tissue may be fresh or frozen. In some embodiments, the tissue sample may be fixed and embedded in paraffin. The tissue sample may be fixed or otherwise preserved by conventional methodology; the choice of a fixative may be determined by the purpose for which the tissue is to be histologically stained or otherwise analyzed. The length of fixation may depend upon the size of the tissue sample and the fixative used. For example, neutral buffered formalin, Bouin's or paraformaldehyde, may be used to fix or preserve a tissue sample.

In some embodiments, the tissue sample may be first fixed and then dehydrated through an ascending series of alcohols, infiltrated and embedded with paraffin or other sectioning media so that the tissue sample may be sectioned. In an alternative embodiment, a tissue sample may be sectioned and subsequently fixed. In some embodiments, the tissue sample may be embedded and processed in paraffin. Examples of paraffin that may be used include, but are not limited to, Paraplast, Broloid, and Tissuecan. Once the tissue sample is embedded, the sample may be sectioned by a microtome into sections that may have a thickness in a range of from about three microns to about five microns. Once sectioned, the sections may be attached to slides using adhesives. Examples of slide adhesives may include, but are not limited to, silane, gelatin, poly-L-lysine. In embodiments, if paraffin is used as the embedding material, the tissue sections may be deparaffinized and rehydrated in water. The tissue sections may be deparaffinized, for example, by using organic agents (such as, xylenes or gradually descending series of alcohols).

In some embodiments, aside from the sample preparation procedures discussed above, the tissue section may be subjected to further treatment prior to, during, or following immunohistochemistry. For example, in some embodiments, the tissue section may be subjected to epitope retrieval methods, such as, heating of the tissue sample in citrate buffer. In some embodiments, a tissue section may be optionally subjected to a blocking step to minimize any non-specific binding.

Following the preparation of the tissue sample, a probe solution (e.g., labeled-antibody solution in an IHC procedure) may be contacted with the tissue section for a sufficient period of time and under conditions suitable for binding of binder to the target (e.g., antigen in an IHC procedure). As described earlier, two detection methods may be used: direct or indirect. In a direct detection, a signal generator-labeled primary antibody (e.g., fluorophore-labeled primary antibody) may be incubated with an antigen in the tissue sample, which may be visualized without further antibody interaction. In an indirect detection, an unconjugated primary antibody may be incubated with an antigen and then a labeled secondary antibody may bind to the primary antibody. Signal amplification may occur as several secondary antibodies may react with different epitopes on the primary antibody. In embodiments where the secondary antibody may be conjugated to an enzymatic label, a chromogenic or fluorogenic substrate may be added to provide visualization of the antigen. In some embodiments two or more (at most four) primary antibodies (labeled or unlabeled) may be contacted with the tissue sample. Unlabeled antibodies may be then contacted with the corresponding labeled secondary antibodies.

Observing a First Signal from the First Probe

A signal from the signal generator in the probe may be detected using a detection system. The nature of the detection system used may depend upon the nature of the signal generators used. The detection system may include an electron spin resonance (ESR) detection system, a charge coupled device (CCD) detection system (e.g., for radioisotopes), a fluorescent detection system, an electrical detection system, a photographic film detection system, a chemiluminescent detection system, an enzyme detection system, an atomic force microscopy (AFM) detection system (for detection of microbeads), a scanning tunneling microscopy (STM) detection system (for detection of microbeads), an optical detection system, a near field detection system, or a total internal reflection (TIR) detection system.

One or more of the aforementioned techniques may be used to observe one or more characteristics of a first signal from a first signal generator (present in the first probe). In some embodiments, signal intensity, signal wavelength, signal location, signal frequency, or signal shift may be determined using one or more of the aforementioned techniques. In some embodiments, one or more aforementioned characteristics of the signal may be observed, measured, and recorded. In some embodiments, a signal generator may include a fluorophore and fluorescence wavelength or fluorescent intensity may be determined using a fluorescence detection system. In some embodiments, a signal may be observed in situ, that is, a signal may be observed directly from the signal generator associated through the binder to the target in the biological sample. In some embodiments, a signal from the signal generator may be analyzed within the biological sample, obviating the need for separate array-based detection systems.

In some embodiments, observing a signal may include capturing an image of the biological sample. In some embodiments, a microscope connected to an imaging device may be used as a detection system, in accordance with the methods disclosed herein. In some embodiments, a signal generator (such as, fluorophore) may be excited and the signal (such as, fluorescence signal) obtained may be observed and recorded in the form of a digital signal (for example, a digitalized image). The same procedure may be repeated for different signal generators (if present) that are bound in the sample using the appropriate fluorescence filters. Applying a Chemical Agent to Modify the First Signal A chemical agent may be applied to the biological sample to modify the signal. In some embodiments, signal modification may include one or more of a change in signal characteristic, for example, a decrease in intensity of signal, a shift in the signal peak, a change in the resonant frequency, or cleavage (removal) of the signal generator resulting in signal removal.

In some embodiments, a chemical agent may be in the form of a solution and the biological sample may be contacted with the chemical agent solution for a predetermined amount of time. The concentration of the chemical agent solution and the contact time may be dependent on the type of signal modification desired. In some embodiments, the contacting conditions for the chemical agent may be selected such that the binder, the target, the biological sample, and binding between the binder and the target may not be affected. In some embodiments, a chemical agent may only affect the signal generator and the chemical agent may not affect the target/binder binding or the binder integrity. Thus by way of example, a binder may include a primary antibody or a primary antibody/secondary combination. A chemical agent according to the methods disclosed herein may only affect the signal generator, and the primary antibody or primary antibody/secondary antibody combination may essentially remain unaffected. In some embodiments, a binder (such as, a primary antibody or primary antibody/secondary antibody combination) may remain bound to the target in the biological sample after contacting the sample with the chemical agent. In some embodiments, a binder may remain bound to the target in the biological sample after contacting the sample with the chemical agent and the binder integrity may remain essentially unaffected (for example, an antibody may not substantially denature or elute in the presence of a chemical agent).

In some embodiments, a characteristic of the signal may be observed after contacting the sample with a chemical agent to determine the effectiveness of the signal modification. For example, a color may be observed before application of the chemical agent and the color may be absent after application of the chemical agent. In another example, fluorescence intensity from a fluorescent signal generator may be observed before contacting with the chemical agent and after contacting with the chemical agent. In some embodiments, a decrease in signal intensity by a predetermined amount may be referred to as signal modification. In some embodiments, modification of the signal may refer to a decrease in the signal intensity by an amount in a range of greater than about 50 percent. In some embodiments, modification of the signal may refer to a decrease in the signal intensity by an amount in a range of greater than about 60 percent. In some embodiments, modification of the signal may refer to a decrease in the signal intensity by an amount in a range of greater than about 80 percent.

Contacting the Sample with a Subsequent Probe and Binding the to a Subsequent Target The biological sample may be contacted with a second probe using one or more procedures described herein above for the first probe. The second probe may be capable of binding to target different from the target bound by the first probe. In embodiments where a plurality of probes may be contacted with the biological sample in the first probe contact step, the second probe may be capable of binding a target different from the targets bound by the first probe set. In some embodiments, a biological sample may be contacted with a plurality of probes in the second probe contact step.

Observing a Second Signal from a Subsequent Probe.

One or more detection methods described hereinabove may be used to observe one or more characteristics of a subsequent (e.g., second, third, etc.) signal from a second signal generator (present in the subsequent probe). In some embodiments, signal intensity, signal wavelength, signal location, signal frequency, or signal shift may be determined using one or more of the aforementioned techniques. Similar to the first signal, a subsequent signal (for example, a fluorescence signal) obtained may be recorded in the form of a digital signal (for example, a digitalized image). In some embodiments, observing a subsequent signal may also include capturing an optical image of the biological sample.

Contacting the Sample with One or More Morphological Stain

In some embodiments, a biological sample may include a cell or a tissue, and the sample may be contacted with a morphological stain before, during, or after the contacting step with the first probe or second probe. A morphological stain may include a dye that may stain different cellular components, in order to facilitate identification of cell type or disease status. In some embodiments, the morphological stain may be readily distinguishable from the signal generators in the first probe and the second probe, that is, the stain may not emit signal that may overlap with signal from the first probe or the second probe. For example, for a fluorescent morphological stain, the signal from the morphological stain may not auto fluoresce in the same wavelength as the fluorophores used in the first probe or the second probe.

A morphological stain may be contacted with the biological sample before, during, or after, any one of the aforementioned steps. In some embodiments, a morphological stain may be contacted with biological sample along with the first probe. In some embodiments, a morphological stain may be contacted with the biological sample before contacting the sample with a chemical agent and after physically binding the first probe to the target. In some embodiments, a morphological stain may be contacted with a biological sample after contacting the sample with a chemical agent and modifying the signal. In some embodiments, a morphological stain may be contacted with a biological sample along with the second probe. In some embodiments, a biological sample may be contacted with the morphological stain after binding the second probe to the target. In some embodiments, a morphological stain may be stable towards a chemical agent, that is, the signal generating properties of the morphological stain may no be substantially affected by the chemical agent. In some embodiments, where a biological sample may be stained with a probe and a morphological stain at the same time, application of chemical agent to modify the signal from the probe may not modify the signal from the morphological stain.

In some embodiments, chromophores, fluorophores, or enzyme/enzyme substrates may be used as morphological stains. Suitable examples of chromophores that may be used as morphological stains (and their target cells, subcellular compartments, or cellular components) may include, but are not limited to, but are not limited to, Eosin (alkaline cellular components, cytoplasm), Hematoxylin (nucleic acids), Orange G (red blood, pancreas, and pituitary cells), Light Green SF (collagen), Romanowsky-Giemsa (overall cell morphology), May-Grunwald (blood cells), Blue Counterstain (Trevigen), Ethyl Green (CAS) (amyloid), Feulgen-Naphthol Yellow S (DNA), Giemsa (differentially stains various cellular compartments), Methyl Green (amyloid), pyronin (nucleic acids), Naphthol-Yellow (red blood cells), Neutral Red (nuclei), Papanicolaou stain (a mixture of Hematoxylin, Eosin Y, Orange G and Bismarck Brown mixture (overall cell morphology)), Red Counterstain B (Trevigen), Red Counterstain C (Trevigen), Sirius Red (amyloid), Feulgen reagent (pararosanilin) (DNA), Gallocyanin chrom-alum (DNA), Gallocyanin chrom-alum and Naphthol Yellow S (DNA), Methyl Green-Pyronin Y (DNA), Thionin-Feulgen reagent (DNA), Acridine Orange (DNA), Methylene Blue (RNA and DNA), Toluidine Blue (RNA and DNA), Alcian blue (carbohydrates), Ruthenium Red (carbohydrates), Sudan Black (lipids), Sudan IV (lipids), Oil Red-O (lipids), Van Gieson's trichrome stain (acid fuchsin and picric acid mixture) (muscle cells), Masson trichrome stain (hematoxylin, acid fuchsin, and Light Green mixture) (stains collagen, cytoplasm, nucleioli differently), Aldehyde Fuchsin (elastin fibers), or Weigert stain (differentiates reticular and collagenous fibers).

Examples of suitable fluorescent morphological stains (and their target cells, subcellular compartments, or cellular components if applicable) may include, but are not limited to: 4',6-diamidino-2-phenylindole (DAPI) (nucleic acids), Eosin (alkaline cellular components, cytoplasm), Hoechst 33258 and Hoechst 33342 (two bisbenzimides) (nucleic acids), Propidium Iodide (nucleic acids), Spectrum Orange (nucleic acids), Spectrum Green (nucleic acids), Quinacrine (nucleic acids), Fluorescein-phalloidin (actin fibers), Chromomycin A 3 (nucleic acids), Acriflavine-Feulgen reaction (nucleic acid), Auramine O-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein (e.g., histones), ACMA, Quinacrine and Acridine Orange.

Examples of suitable enzymes (and their primary cellular locations or activities) may include, but are not limited to, ATPases (muscle fibers), succinate dehydrogenases (mitochondria), cytochrome c oxidases (mitochondria), phosphorylases (mitochondria), phosphofructokinases (mitochondria), acetyl cholinesterases (nerve cells), lactases (small intestine), acid phosphatases (lysosomes), leucine aminopeptidases (liver cells), dehydrogenases (mitochondria), myodenylate deaminases (muscle cells), NADH diaphorases (erythrocytes), and sucrases (small intestine).

Reiteration of the Contacting, Binding, and Observing Steps

In some embodiments, after contacting the sample with a subsequent (e.g., second, third, etc.) probe, agent modification and subsequent probe administration may be repeated multiple times. In some embodiments, after observing a second signal from the second probe, the biological sample may be contacted with a chemical agent to modify the signal from the second probe. Furthermore, a third probe may be contacted with the biological sample, wherein the third probe may be capable of binding a target different from the first and the second probes. Likewise, a signal from the third probe may be observed followed by application of chemical agent to modify the signal. The contacting, binding, and observing steps may be repeated iteratively multiple times using an $n^{th}$ probe capable of binding to additional targets to provide the user with information about a variety of targets using a variety of probes and/or signal generators.

In some embodiments, a series of probes may be contacted with the biological sample in a sequential manner to obtained a multiplexed analysis of the biological sample. In some embodiments, a series of probe sets (including at most 4 probes in one set) may be contacted with the biological sample in a sequential manner to obtained a multiplexed analysis of the biological sample. Multiplexed analysis generally refers to analysis of multiple targets in a biological sample using the same detection mechanism.

Correlating the First Signal and the Subsequent Signals

In some embodiments, a first signal, a second signal, or both first signal and the second signal may be analyzed to obtain information regarding the biological sample. For example, in some embodiments, a presence or absence of a first signal may indicate the presence or absence of the first target (capable of binding to the first binder) in the biological sample. Similarly, the presence or absence of a second signal may indicate the presence or absence of the second target (capable of binding to the second binder in the biological sample). In embodiments where multiple targets may be analyzed using a plurality of probes, the presence or absence of a particular signal may indicate the presence or absence of corresponding target in the biological sample.

In some embodiments, an intensity value of a signal (for example, fluorescence intensity) may be measured and may be correlated to the amount of target in the biological sample. A correlation between the amount of target and the signal intensity may be determined using calibration standards. In some embodiment, intensity values of the first and second signals may be measured and correlated to the respective target amounts. In some embodiments, by comparing the two signal intensities, the relative amounts of the first target and the second target (with respect to each other or with respect to a control) may be ascertained. Similarly, where multiple targets may be analyzed using multiple probes, relative amounts of different targets in the biological sample may be determined by measuring different signal intensities. In some embodiments, one or more control samples may be used as described hereinabove. By observing a presence or absence of a signal in the samples (biological sample of interest versus a control), information regarding the biological sample may be obtained. For example by comparing a diseased tissue sample versus a normal tissue sample, information regarding the targets present in the diseased tissue sample may be obtained. Similarly by comparing signal intensities between the samples (i.e., sample of interest and one or more control), information regarding the expression of targets in the sample may be obtained.

In some embodiments, a location of the signal in the biological sample may be observed. In some embodiments, a localization of the signal in the biological signal may be observed using morphological stains. In some embodiments relative locations of two or more signals may be observed. A location of the signal may be correlated to a location of the target in the biological sample, providing information regarding localization of different targets in the biological sample. In some embodiments, an intensity value of the signal and a location of the signal may be correlated to obtain information regarding localization of different targets in the biological sample. For examples certain targets may be expressed more in the cytoplasm relative to the nucleus, or vice versa. In some embodiments, information regarding relative localization of targets may be obtained by comparing location and intensity values of two or more signals.

In some embodiments, one or more of the observing or correlating step may be performed using computer-aided means. In embodiments where the signal(s) from the signal generator may be stored in the form of digital image(s), computer-aided analysis of the image(s) may be conducted. In some embodiments, images (e.g., signals from the probe(s) and morphological stains) may be overlaid using computer-aided superimposition to obtain complete information of the biological sample, for example topological and correlation information.

In some embodiments, one or more of the aforementioned steps (a) to (g) may be automated and may be performed using automated systems. In some embodiments, all the steps (a) to (g) may be performed using automated systems.

The methods disclosed herein may find applications in analytic, diagnostic, and therapeutic applications in biology and in medicine. In some embodiments, the methods disclosed herein may find applications in histochemistry, particularly, immunohistochemistry. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biologically sample.

EXAMPLES

The following examples are intended only to illustrate methods and embodiments in accordance with the invention, and as such should not be construed as imposing limitations upon the claims.

The following examples 1-6 illustrate embodiments in which labels are chemically destroyed by oxidizing agents, nucleophiles or changes in pH. Oxidizing agents used are hydrogen peroxide ($H_2O_2$) and sodium periodate ($NaIO_4$). Changes in pH are obtained using a base like sodium hydroxide (NaOH). Tris(2-carboxyethyl)phosphate created in situ by dissolving TCEP.HCl in base is a nucleophile. Labels include cyanine dyes, such as, Cy3, Cy5, and Cy7 and nuclear labels, such as, 4',6-diamidino-2-phenylindole (DAPI). Selective destruction of labels may be obtained by varying the concentration, type, and time of exposure to the oxidizing agent or base.

Example 1

Selective Oxidation Using Hydrogen Peroxide of Cyanine Dyes without Affecting DAPI A solution of hydrogen peroxide ($H_2O_2$) was prepared in a sodium bicarbonate buffer by mixing 1 volume of 1 molar (1M) sodium biocarbonate, 3 volumes of water, and 1 volume of 30 percent (v/v) hydrogen peroxide. pH of sodium bicarbonate was adjusted to a pH 10 using sodium hydroxide, prior to mixing with hydrogen peroxide.

Three separate solutions of cyanine dyes: Cy3, Cy5, and Cy7 were prepared in water at a concentration of about 2 micromolar (2 μM). An aliquot of a cyanine dye solution was mixed with an aliquot of the $H_2O_2$ solution to prepare a sample solution with a final concentration of about 3 volume percent $H_2O_2$ and 1 micromolar (1 μM) cyanine dye (Samples 1 (Cy3), 2 (Cy5), and 3 (Cy7)). A 1 micromolar (1 μM) cyanine dye solution in water (without $H_2O_2$) was used as a control.

Figure 2:
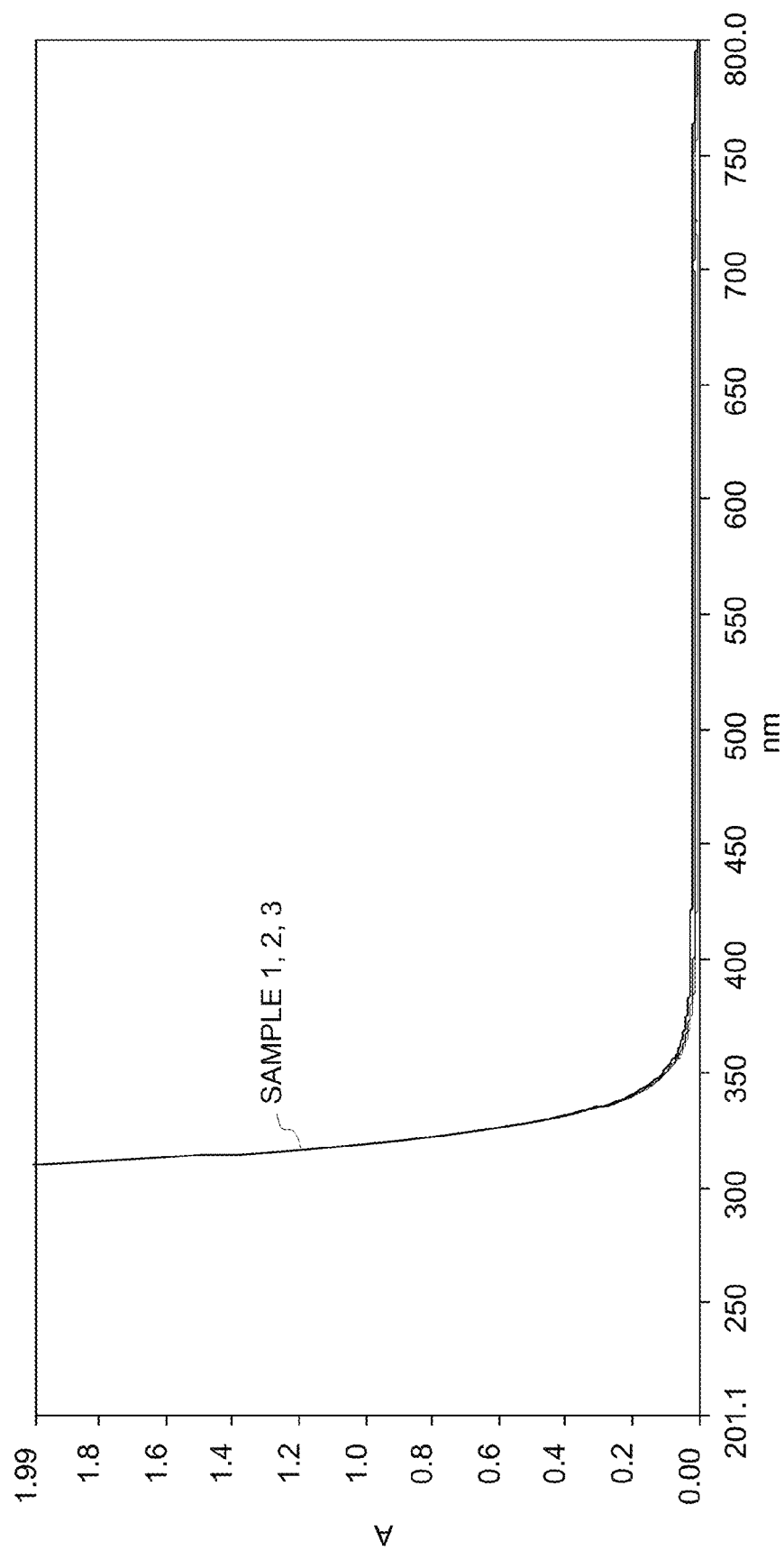
FIG. 2 is the absorbance spectra for Samples 1, 2, and 3 as a function of wavelength.

Oxidation reaction of the cyanine dye was monitored by measuring absorbance spectrum of the dye on an ultraviolet/visible (UV/Vis) spectrophotometer as a function of time. FIG. 1 shows the absorbance spectra of Sample 1 as a function of wavelength, after duration of 10 minutes and 15 minutes. The absorbance value decreased considerably when compared with the control. FIG. 2 shows the absorbance values for Samples 1, 2, and 3 as a function of wavelength. The absorbance of the Samples 1, 2 and 3 reduced to zero after a duration of time exhibiting chemical destruction of the dye by $H_2O_2$. The time duration for the Samples 1, 2 and 3 was different for the different dye: 19 minutes for Sample 1, 15 minutes for Sample 2, and 3 minutes for Sample 3.

A solution of 4',6-diamidino-2-phenylindole (DAPI) was prepared in water at a concentration of about 57 μM. An aliquot of DAPI solution was mixed with an aliquot of the $H_2O_2$ solution to prepare a solution with a final concentration of about 3 volume percent $H_2O_2$ and 10 micrograms/milliliters DAPI (Sample 4). A 10 micrograms/milliliters DAPI solution in water (without $H_2O_2$) was used as a control.

Figure 3:
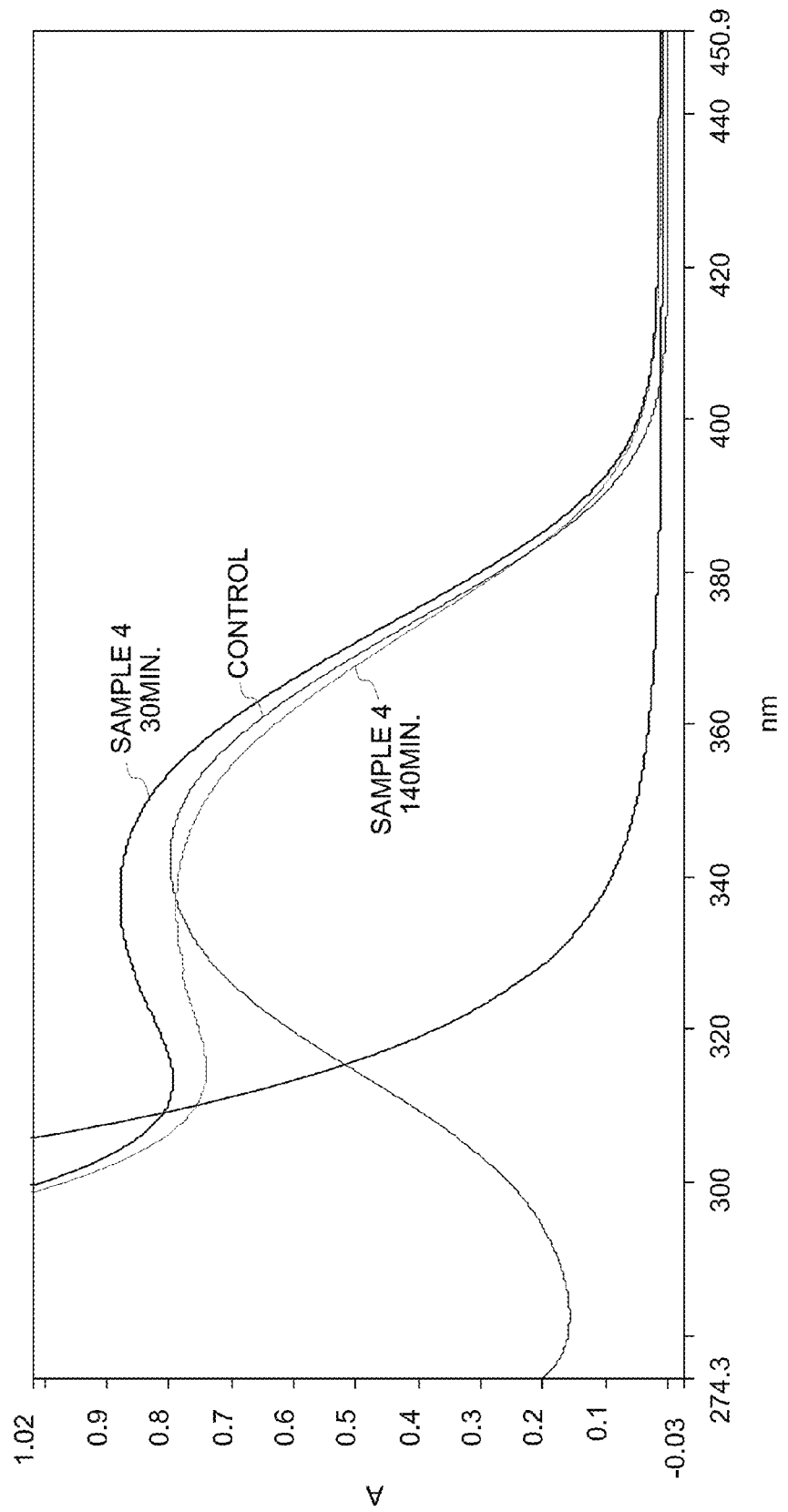
FIG. 3 is the absorbance spectra of Sample 4 as a function of wavelength, after 30 minutes and 140 minutes.

Oxidation reaction of DAPI was monitored by measuring absorbance spectrum of Sample 4 as a function of time. FIG. 3 shows the absorbance spectra of Sample 4 as a function of wavelength, after duration of 30 minutes and 140 minutes. The absorbance value of Sample 4 did not vary much even after a period of 140 minutes and was in the same range as the control, exhibiting no significant effect of $H_2O_2$ on DAPI.

Example 2

Selective Oxidation (Using Sodium Periodate) of Cyanine Dyes without Affecting DAPI A solution of sodium periodate ($NaIO_4$) was prepared by mixing a 0.2 molar solution of $NaIO_4$ in 0.1× phosphate buffer saline (PBS). Three separate solutions of cyanine dyes, Cy3, Cy5, and Cy7 were prepared in water at a concentration of about 2 micromolar (2 μM). An aliquot of a cyanine dye solution was mixed with an aliquot of the $NaIO_4$ solution to prepare a solution with a final concentration of about 0.1 molar (1 μM) $NaIO_4$ and 1 micromolar (1 μM) cyanine dye (Samples 5 (Cy3), 6 (Cy5), and 7 (Cy7)). A 1 micromolar (1 μM) cyanine dye solution in water (without $NaIO_4$) was used as a control.

Figure 4:
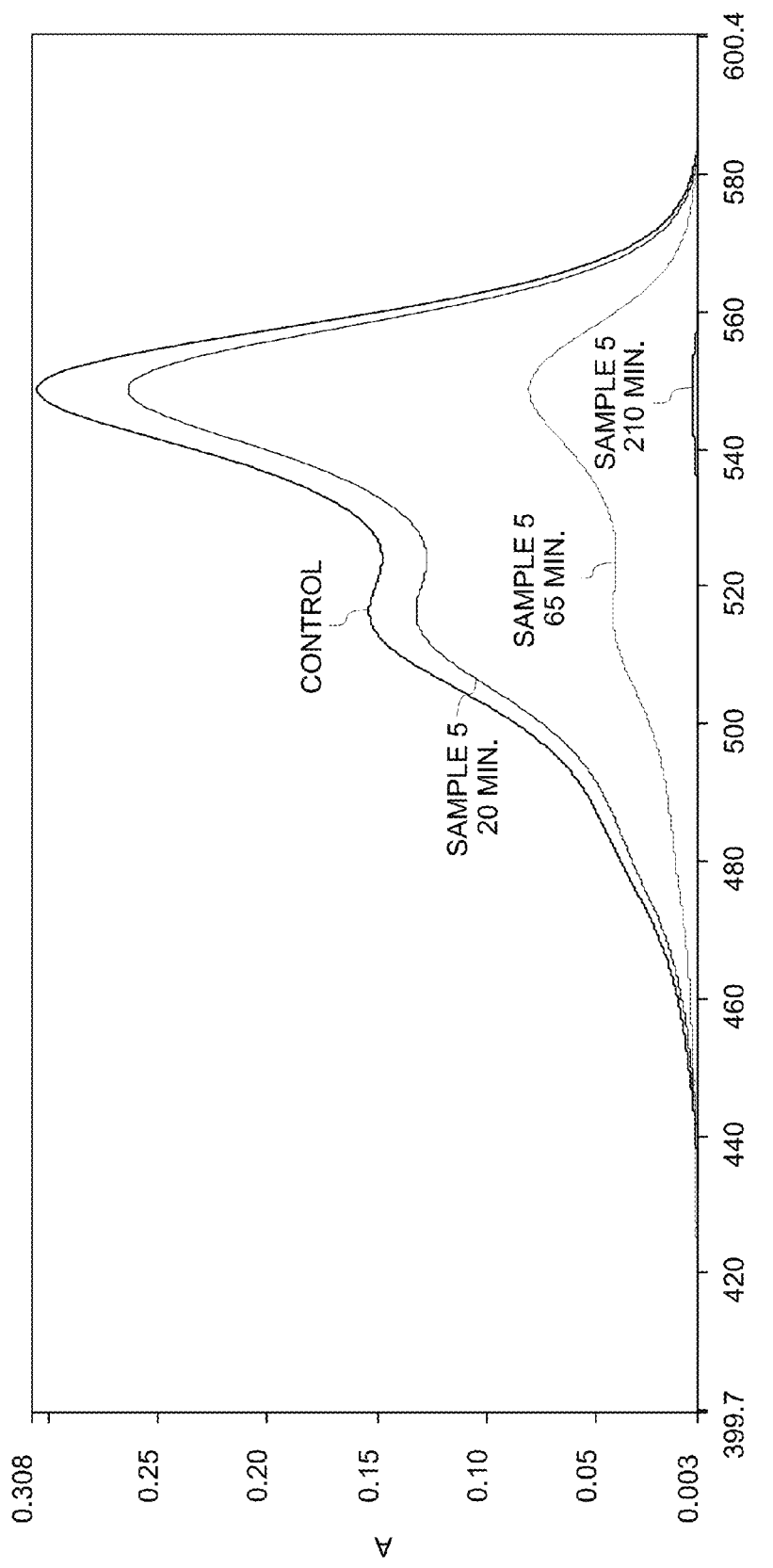
FIG. 4 is the absorbance spectra of Sample 5 as a function of wavelength, after 20 minutes, 60 minutes, and 210 minutes.
Figure 5:
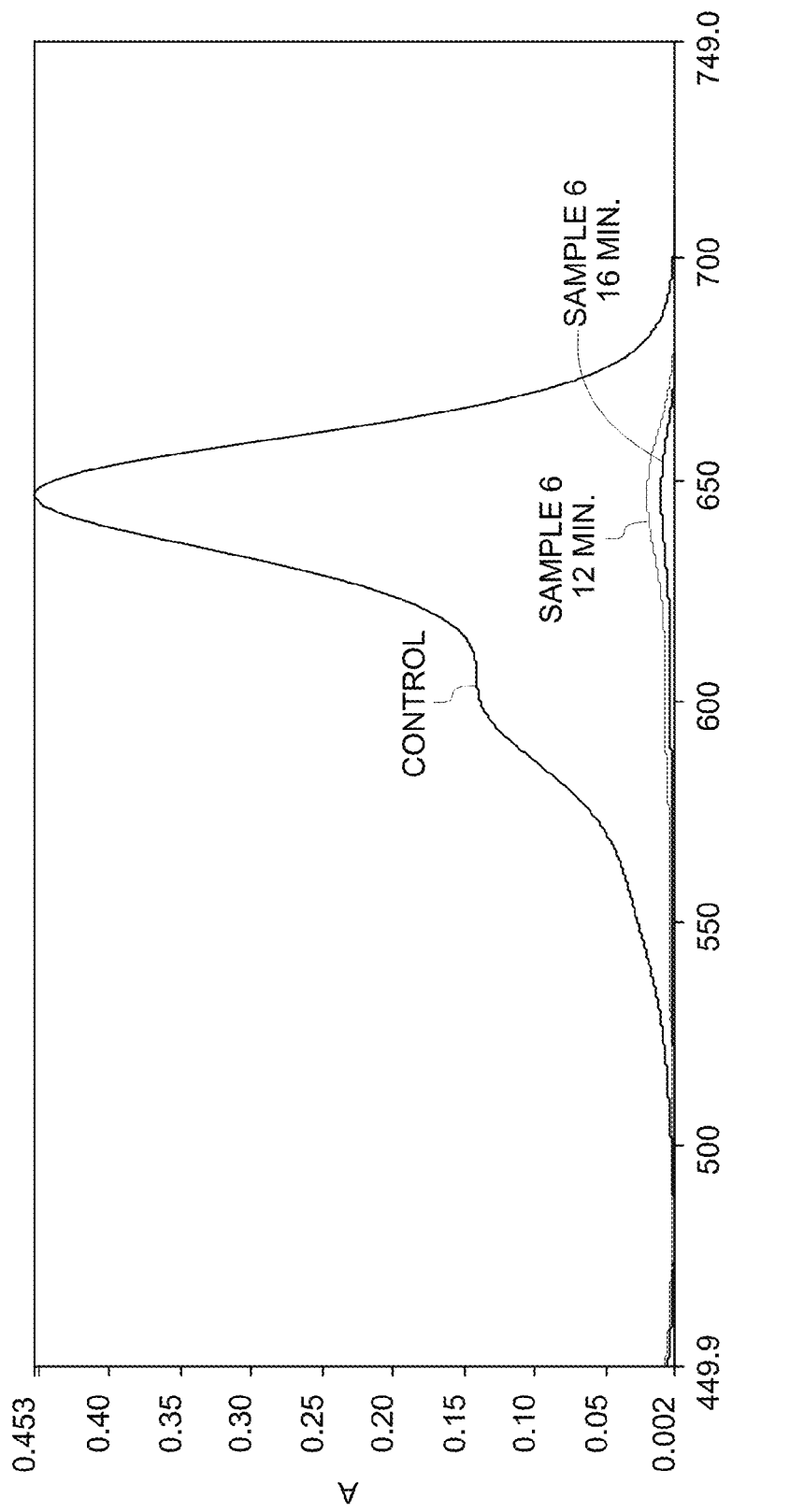
FIG. 5 is the absorbance spectra of Sample 6 as a function of wavelength, after 12 minutes and 16 minutes.

Oxidation reaction of the cyanine dye was monitored by measuring absorbance spectrum of the dye on an ultraviolet/visible (UV/Vis) spectrophotometer as a function of time. FIG. 4 shows the absorbance spectra of Sample 5 as a function of wavelength, after duration of 20 minutes, 60 minutes and 210 minutes. The absorbance value decreased as function of time when compared with the control. Complete absorbance loss was observed after 210 minutes for Sample 5. FIG. 5 shows the absorbance spectra of Sample 6 as a function of wavelength, after duration of 12 minutes and 16 minutes. The absorbance value decreased as function of time when compared with the control. Complete absorbance loss was observed rapidly, after 16 minutes.

A solution of 4',6-diamidino-2-phenylindole (DAPI) was prepared in water at a concentration of about 57 μM. An aliquot of DAPI solution was mixed with an aliquot of the $NaIO_4$ solution to prepare a solution with a final concentration of about 0.1M $NaIO_4$ and 10 micrograms/milliliters DAPI (Sample 8). A 10 micrograms/milliliters DAPI solution in water (without $NaIO_4$) was used as a control.

Figure 6:
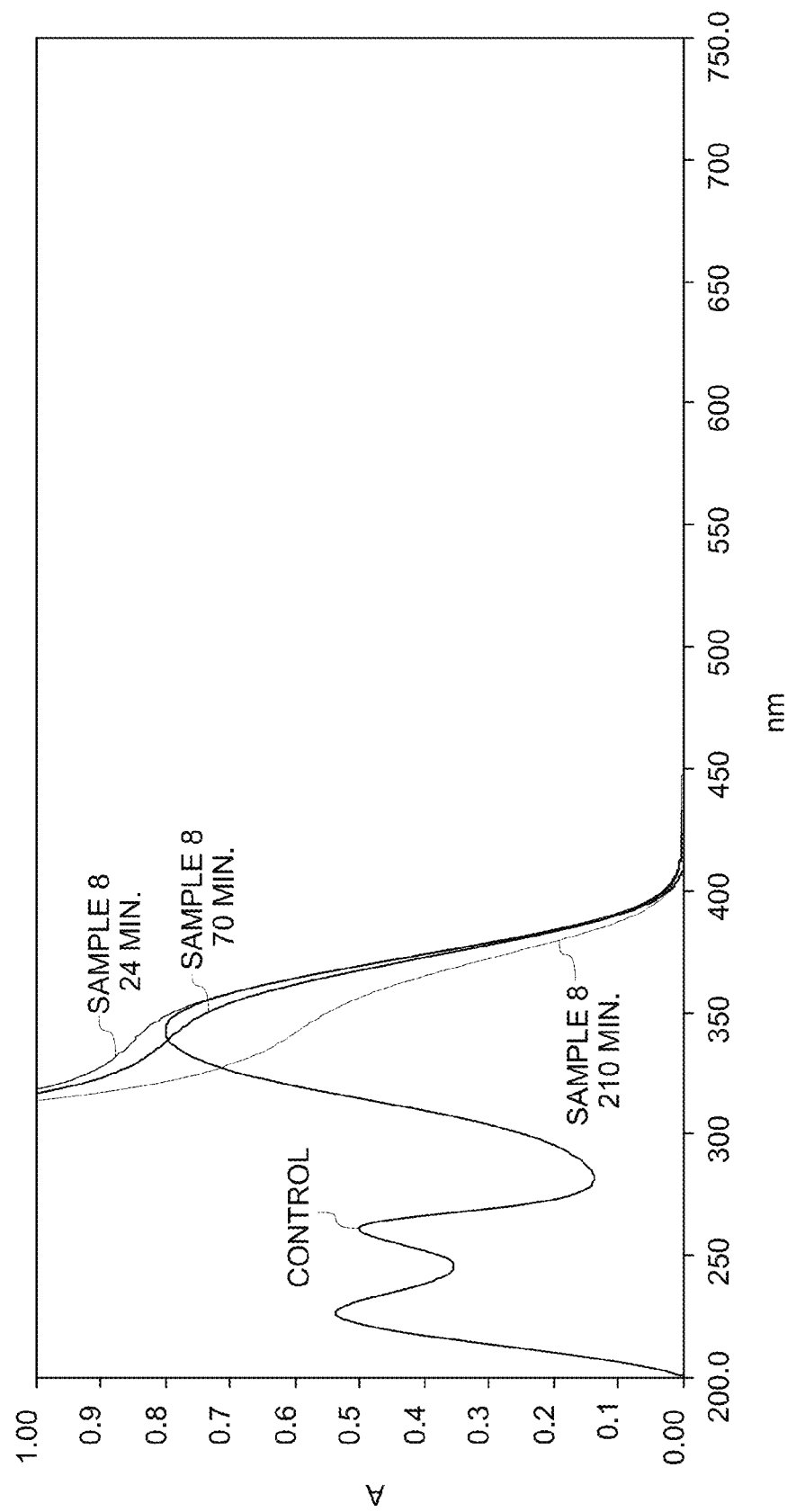
FIG. 6 is the absorbance spectra of Sample 8 as a function of wavelength, after 22 minutes, 70 minutes, and 210 minutes.

Oxidation reaction of DAPI was monitored by measuring absorbance spectrum of Sample 8 as a function of time. FIG. 6 shows the absorbance spectra of Sample 8 as a function of wavelength, after duration of 22 minutes, 70 minutes and 210 minutes. The absorbance value of Sample 8 did not vary much even after a period of 210 minutes and a significant amount of DAPI remained intact when compared to the control.

Example 3

Selective Destruction (Using Sodium Hydroxide Base) of Cyanine Dyes Without Affecting DAPI A NaOH solution was prepared at a concentration of 0.1M and 1M. Three separate solutions of cyanine dyes, Cy3, Cy5, and Cy7 were prepared in water at a concentration of 2 μM. An aliquot of a cyanine dye solution was mixed with an aliquot of the NaOH solution of two different concentrations of NaOH: 0.1M NaOH (Samples 9a, 10a, and 11a) and 1M NaOH (Samples 9b, 10b, and 11b). A 1 µM cyanine dye solution in water (without NaOH) was used as a control.

Figure 7:
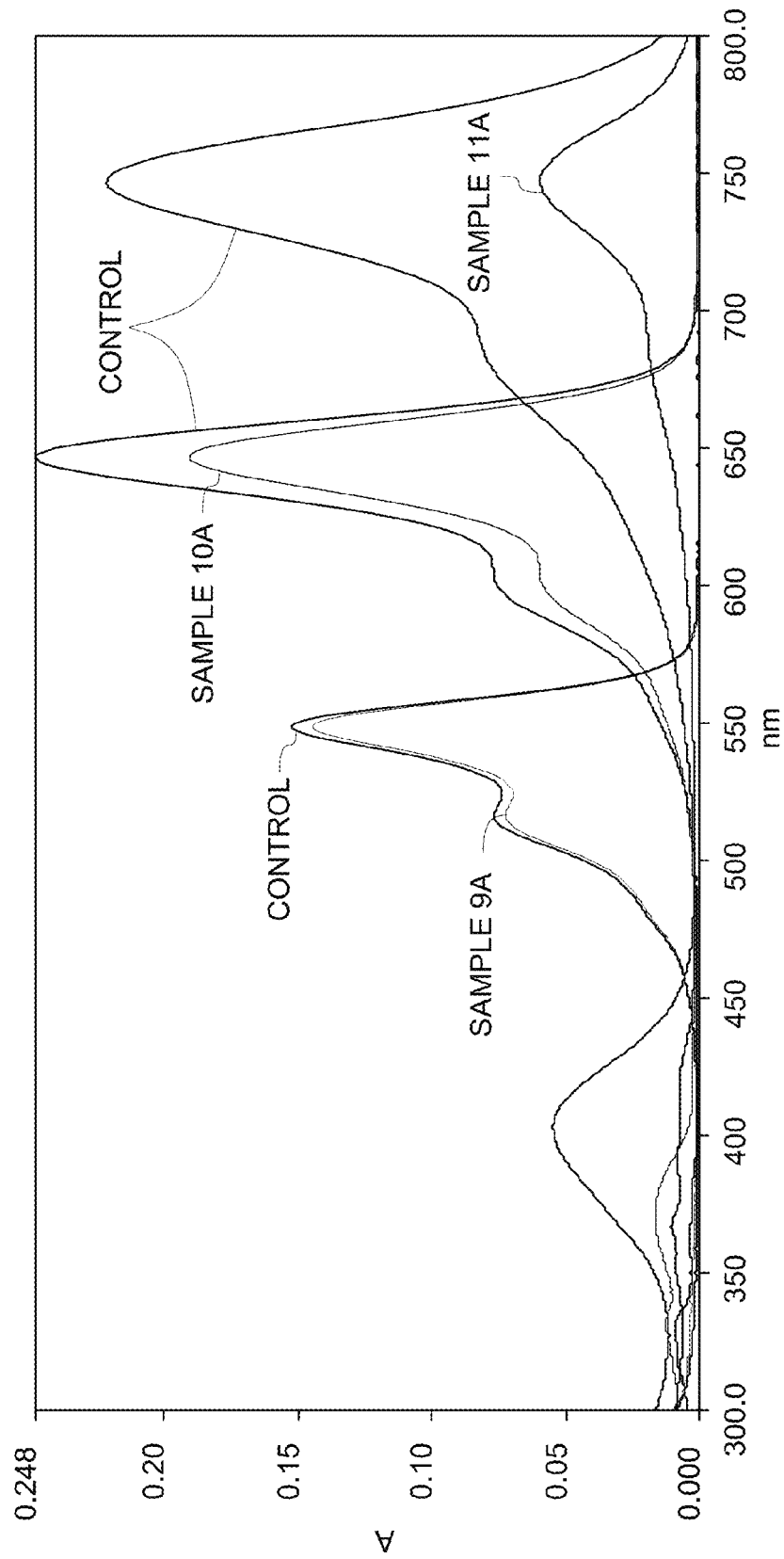
FIG. 7 is the absorbance spectra of Samples 9a, 10a, and 11a as a function of wavelength.
Figure 8:
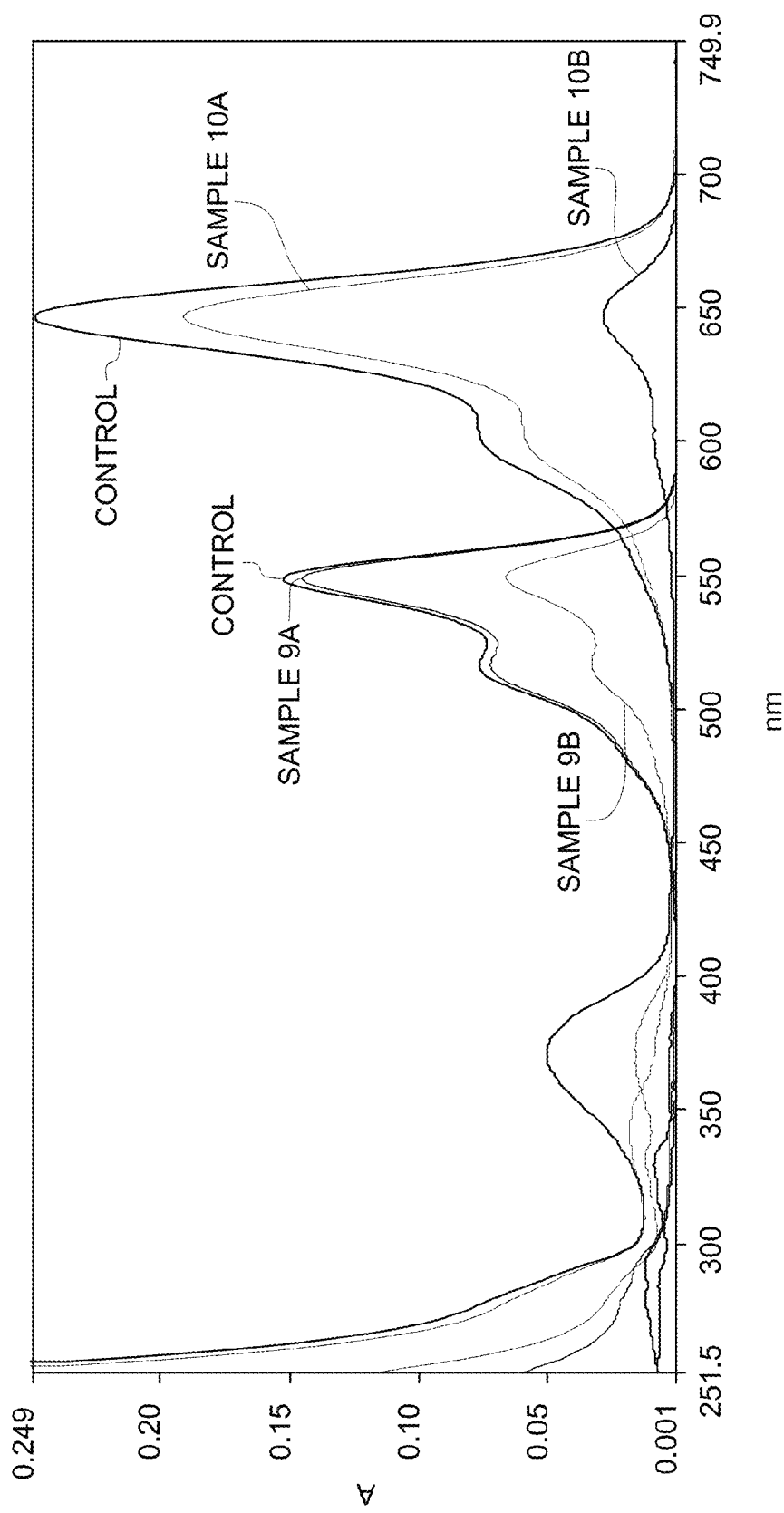
FIG. 8 is the absorbance spectra of Samples 9b and 10b as a function of wavelength.

Base destruction of the dye was monitored by measuring absorbance spectrum of the samples as a function of time. FIG. 7 shows the absorbance spectra of Samples 9a, 10a, and 11a as a function of wavelength, after duration of less than 5 minutes. The absorbance value of Sample 9a did not vary much and a significant amount of Cy3 remained intact when compared to the control. Sample 10a showed a 20 percent decomposition of the Cy5 dye, while Sample 11a showed a 70 percent decomposition of the Cy7 dye using 0.1 M NaOH. FIG. 8 shows the absorbance spectra of Samples 9b and 10b as a function of wavelength, after duration of less than 5 minutes. Sample 9b showed a 50 percent decomposition of the Cy3 dye, while Sample 10b showed an 80 percent decomposition of the Cy5 dye using 1 M NaOH.

Figure 9:
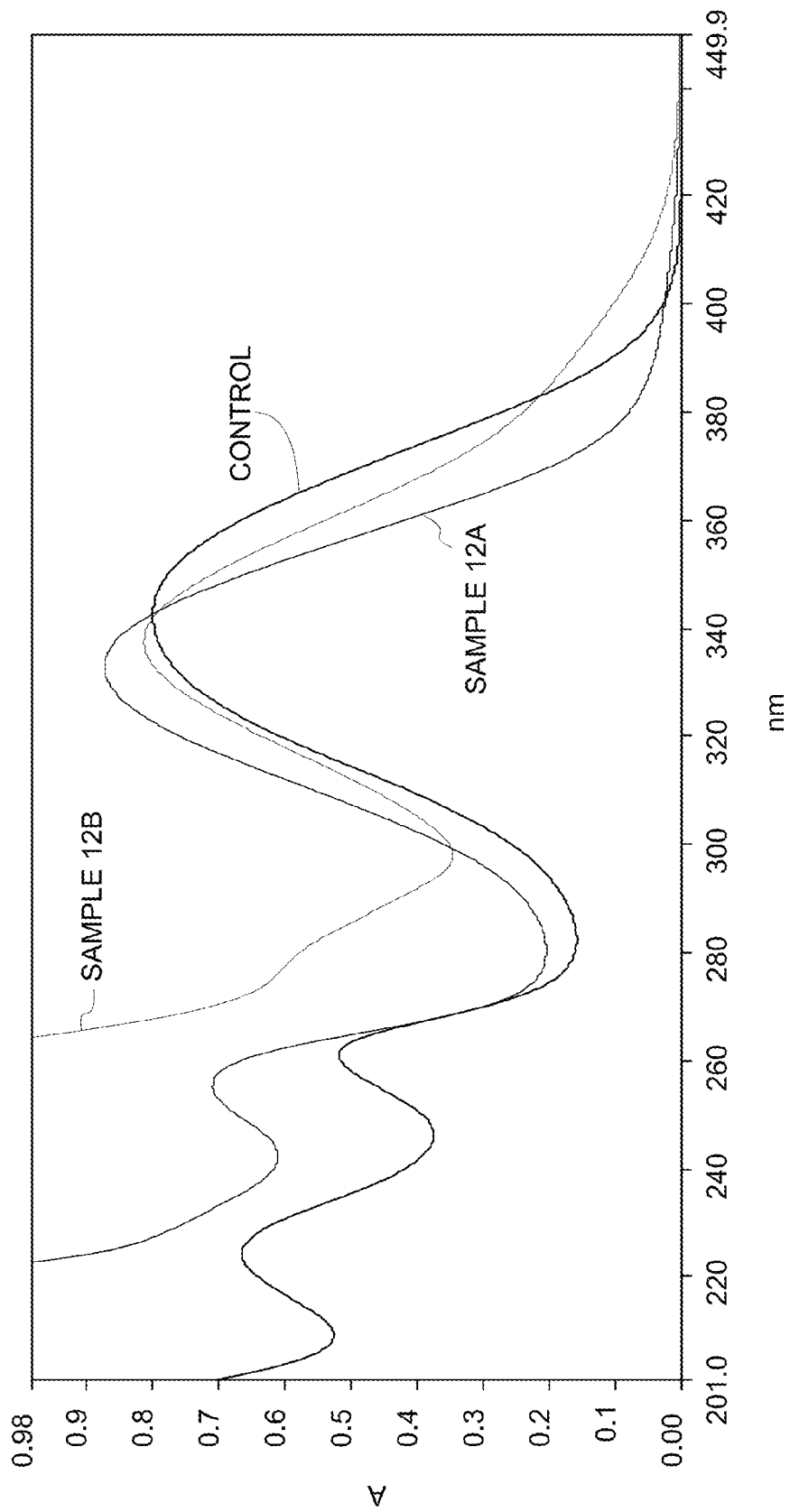
FIG. 9 is the absorbance spectra of Samples 12a and 12b as a function of wavelength.

A solution of 4',6-diamidino-2-phenylindole (DAPI) was prepared in water at a concentration of about 57 µM. An aliquot of DAPI solution was mixed with an aliquot of the NaOH solution of two different concentrations 0.1M NaOH (Samples 12a) and 1M NaOH (Samples 12b). A 10 micrograms/milliliters DAPI dye solution in water (without NaOH) was used as a control. Base destruction of DAPI was monitored by measuring absorbance spectrum of Samples 12a and 12b as a function of time. FIG. 9 shows the absorbance spectra of Samples 12a and 12b as a function of wavelength. The absorbance value of the samples did not vary much and a significant amount of DAPI remained intact when compared to the control.

Example 4

Selective Destruction of Cy5 and Cy7 dyes Without Affecting Cy3

A 5 percent (w/v) solution of a nucleophile was prepared by mixing tris[2-carboxyethyl]-phosphine hydrochloride (TCEP.HCl) in 1M sodium biocarbonate buffer (final pH 7.7). Three separate solutions of cyanine dyes, Cy3, Cy5, and Cy7 were prepared in water at a concentration of about 2 µM. An aliquot of a cyanine dye solution was mixed with an aliquot of the TCEP.HCl solution to prepare Samples 13 (Cy3), 14 (Cy5), and 15 (Cy7). A 1 µM cyanine dye solution in water (without TCEP.HCl) was used as a control.

Figure 10:
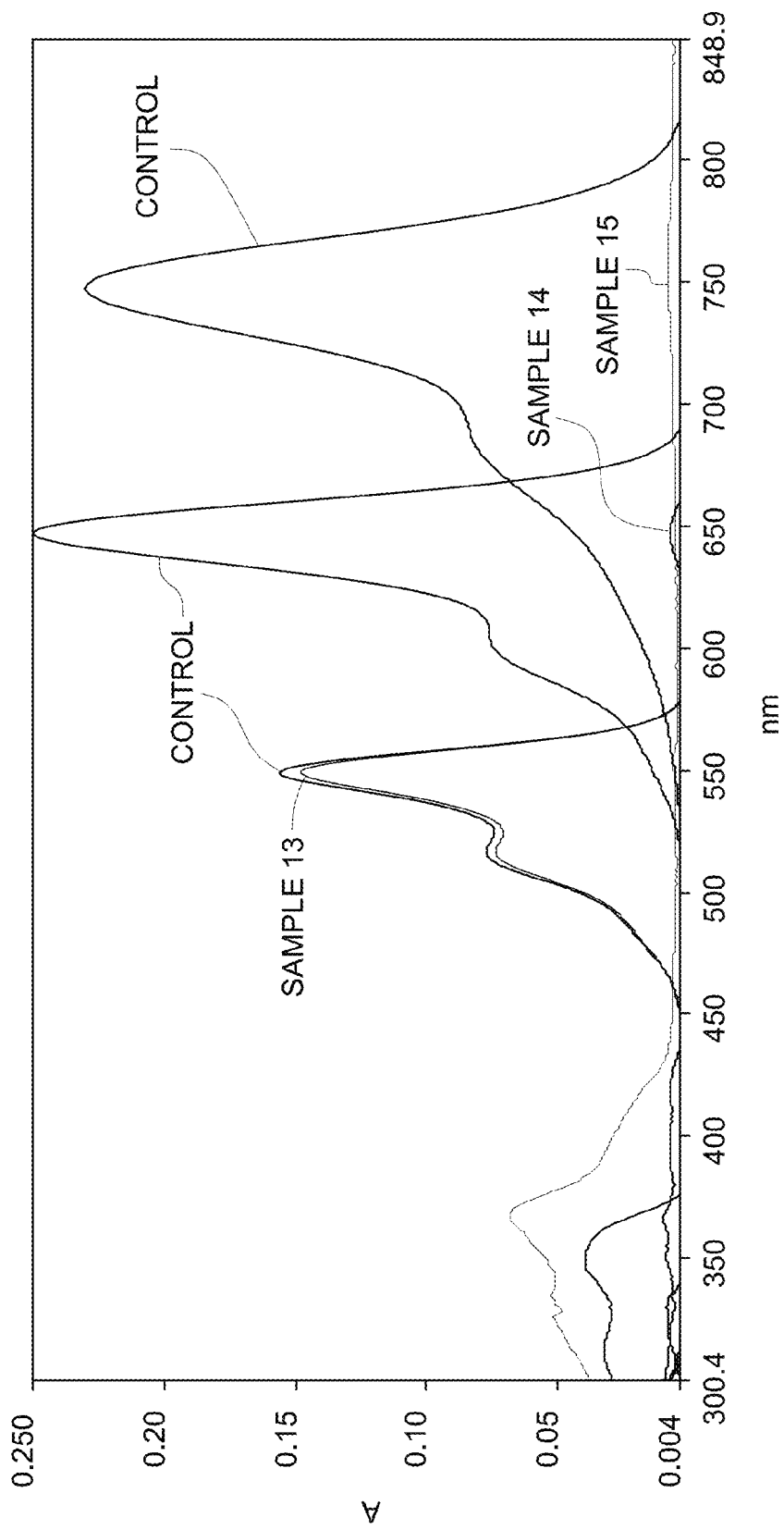
FIG. 10 is the absorbance spectra of Samples 13, 14, and 15 as a function of wavelength.

Destruction of the dye was monitored by measuring absorbance spectrum of the samples as a function of time. FIG. 10 shows the absorbance spectra of Samples 13, 14, and 15 as a function of wavelength. The absorbance value of Sample 13 did not vary much and a significant amount of Cy3 remained intact when compared to the control after duration of 60 minutes. Samples 14 and 15 showed a significant decomposition of the Cy5 and Cy7 dyes after duration of 0.5 minutes.

Example 5

Selective Destruction of Cy7 Dye without Affecting Cy3

A solution of hydrogen peroxide ($H_2O_2$) was prepared in a phosphate buffer saline solution (PBS) by mixing a 6 percent (v/v) solution of $H_2O_2$ in 0.8×PBS (final pH 6.6). Two separate solutions of cyanine dyes, Cy3 and Cy7 were prepared in water at a concentration of about 2 micromolar (2 µM). An aliquot of a cyanine dye solution was mixed with an aliquot of the $H_2O_2$ solution to prepare Samples 16 (Cy3) and 17 (Cy7)). A 1 micromolar (1 µM) cyanine dye solution in water (without $H_2O_2$) was used as a control.

Figure 11:
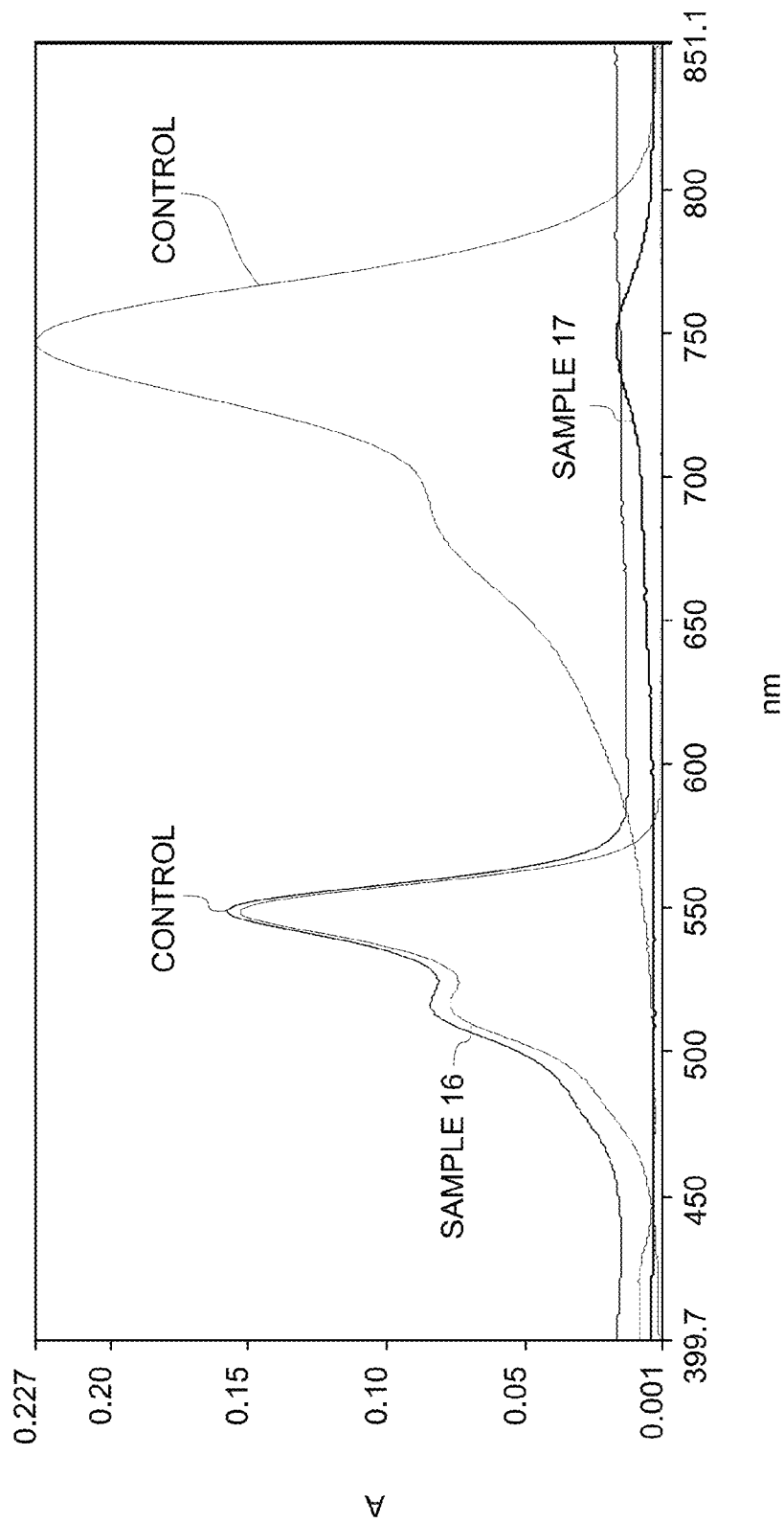
FIG. 11 is the absorbance spectra of Samples 16 and 17 as a function of wavelength.

Destruction of the dye was monitored by measuring absorbance spectrum of the samples as a function of time. FIG. 11 shows the absorbance spectra of Samples 16 and 17 as a function of wavelength. The absorbance value of Sample 16 did not vary much and a significant amount of Cy3 remained intact when compared to the control after duration of 60 minutes. Sample 17 showed a significant decomposition of the Cy7 dye after duration of 60 minutes.

The following examples 7-21 illustrate embodiments of the invention according to which multiple imaging of tissue samples is conducted. Multiple staining is obtained by staining, imaging, chemically destroying the stain, restaining, imaging, and repeating the steps.

Example 6

Preparation of Tissue Samples for Staining

Adult human tissue samples were obtained as tissue slides embedded in paraffin. The tissue samples included slides of colon (Biochain, T2234090), normal breast tissue (Biochain, T2234086), prostate cancer (Biochain, T2235201-1), colon adenocarcinoma (Biochain, T2235090-1), breast tissue microarray (Imgenex, IMH 367, p61), breast TMA (Imegenex IMH 367,p32), and normal prostate (Biochain, T2234201). Paraffin embedded slides of adult human tissue were subjected to an immunohistochemistry protocol to prepare them for staining. The protocol included deparaffinization, rehydration, incubation, and wash. Deparaffinization was carried by washing the slides with Histochoice (or toluene) for a period of 10 minutes and with frequent agitation. After deparaffinization, the tissue sample was rehydrated by washing the slide with ethanol solution. Washing was carried out with three different solutions of ethanol with decreasing concentrations. The concentrations of ethanol used were 90 volume percent, 70 volume percent, and 50 volume percent. The slide was then washed with a phosphate buffer saline (PBS, pH 7.4). Membrane permeabilization of the tissue was carried out by washing the slide with 0.1 weight percent solution of Triton TX-100. Citrate buffer pH 6.0 (Vector Unmasking Solution) was used for antigen retrieval. The slides were exposed to the buffer in a pressure cooker for a period of 15 minutes followed by cooling at room temperature for a period of 20 minutes. The slide was then blocked against nonspecific binding by washing with PBS and 900 microliters of 3 volume percent bovine serum albumin (BSA) for 45 minutes at 37 degrees Celsius. For staining with secondary antibodies (optional), the slide was also blocked with 100 microliters of serum from secondary antibody host species.

Example 7

Conjugation of Antibodies with a Dye

Dye-conjugated antibodies were prepared according to the following procedure. The antibodies used for conjugating and staining included anti proliferating cell nuclear antigen, clone pc10 (Sigma Aldrich, P8825); anti smooth muscle alpha actin (5 mA), clone 1A4 (Sigma, A2547); rabbit anti beta catenin (Sigma, C 2206); mouse anti pan cytokeratin, clone PCK-26 (Sigma, C1801); mouse anti estrogen receptor alpha, clone 1D5 (DAKO, M 7047); beta catenin antibody, clone 15B8 (Sigma, C 7738); goat anti vimentin (Sigma, V4630); cycle androgen receptor clone AR441 (DAKO, M3562); Von willebrand factor 7, keratin 5, keratin 8/18, e-cadherin, Her2/neu, Estrogen receptor, p53, progesterone receptor, beta catenin; donkey anti-mouse (Jackson Immunoresearch, 715-166-150); and donkey anti rabbit (Jackson Immunoresearch, 711-166-152).

A micron YM-10 spin column was wetted with 250 microliters of PBS and the column was spun for 15 minutes. 500 milliliters of the antibody (200 micrograms/milliliters) was pipetted into the wet column The column was spun for 30 minutes at 11000 rpm at 4 degrees Celsius. The concentrated antibody/protein was then transferred into a new tube and spun for 30 seconds to remove the concentrated protein. A coupling buffer solution was then mixed with the concentrated antibody solution. The coupling buffer solution included 1M sodium carbonate (pH between 8-9) and 5 microliters of the buffer was used per 100 microliters of the antibody solution. The antibody and buffer solution was added to 0.01-0.1 milligrams of the cyanine dye. The dye was reconstituted in DMSO to a 10-20-milligrams/milliliter concentration prior to incubating with the antibody. The resulting solution was mixed thoroughly by pipetting and any bubbles formed were removed by spinning the tube. The solution was covered with a foil and incubated at room temperature for a period of about 30-45 minutes. Post incubation the solution was added to YM-10 spin column and spun for 30 minutes at 4 degrees Celsius at 11000 rpm. The solution was washed with PBS and spun to remove any unconjugated dye or antibody. The dye-conjugated antibody solution was then diluted with 50 percent glycerol and stored in a freezer at −20 degrees Celsius.

Example 8

Staining and Imaging of Tissue with Dyes

A slide prepared in Example 6 was incubated with a dye-conjugated antibody prepared in Example 7. Incubation was conducted in 3 percent BSA for 45 minutes at 37 degrees Celsius. After incubation, the slide was subjected to an extensive series of PBS washes. When secondary antibodies (optional) were used, the slide was incubated with a secondary antibody in BSA for 45 minutes at 37 degrees Celsius. After incubation, the slide was subjected to an extensive series of PBS washes. A primary antibody or secondary antibody (optional)-stained slide was optionally counterstained with the morphological stain, DAPI, and cover slipped.

A cover slipped slide was imaged using a camera. The camera used was a monochromatic Leica DFC 350FX monochromatic high-resolution camera mounted in a Leica DMRA2 fluorescent microscope. The magnification used was 20x unless otherwise stated. After image acquisition, the cover slip was removed and the slide was washed with PBS to prepare for signal destruction.

Example 9

Dye Destruction, Staining and Imaging

NaOH solution and $H_2O_2$ solution were used for signal destruction. A NaOH solution was prepared suing 500 microliters of 50 volume percent NaOH and 49.5 milliliters of PBS. The final pH of the NaOH solution was around 11.9-12.5. A $H_2O_2$ solution was prepared by mixing 10 milliliters of 0.5M sodium carbonate (pH 10), 5 milliliters of 30 volume percent $H_2O_2$, and 35 milliliters of water. A slide was placed in the NaOH or $H_2O_2$ solution for 15 minutes with gentle agitation. After 15 minutes, the slide was washed again with PBS, cover slipped and either imaged again (optional) to check the efficacy of the dye destruction or restained and imaged. Restaining and reimaging steps were carried out using the process described in Example 8. Following imaging, a slide was subjected to signal destruction, staining, and imaging cycles, and the process was repeated a multiple number of times. The tissue samples were imaged using 1-9 different antibodies. After imaging with the cyanine series, the slide was optionally stained and imaged with morphological stains H&E.

Example 10

Single Channel Staining and Imaging of a Normal Colon Tissue Using NaOH

Figure 12:
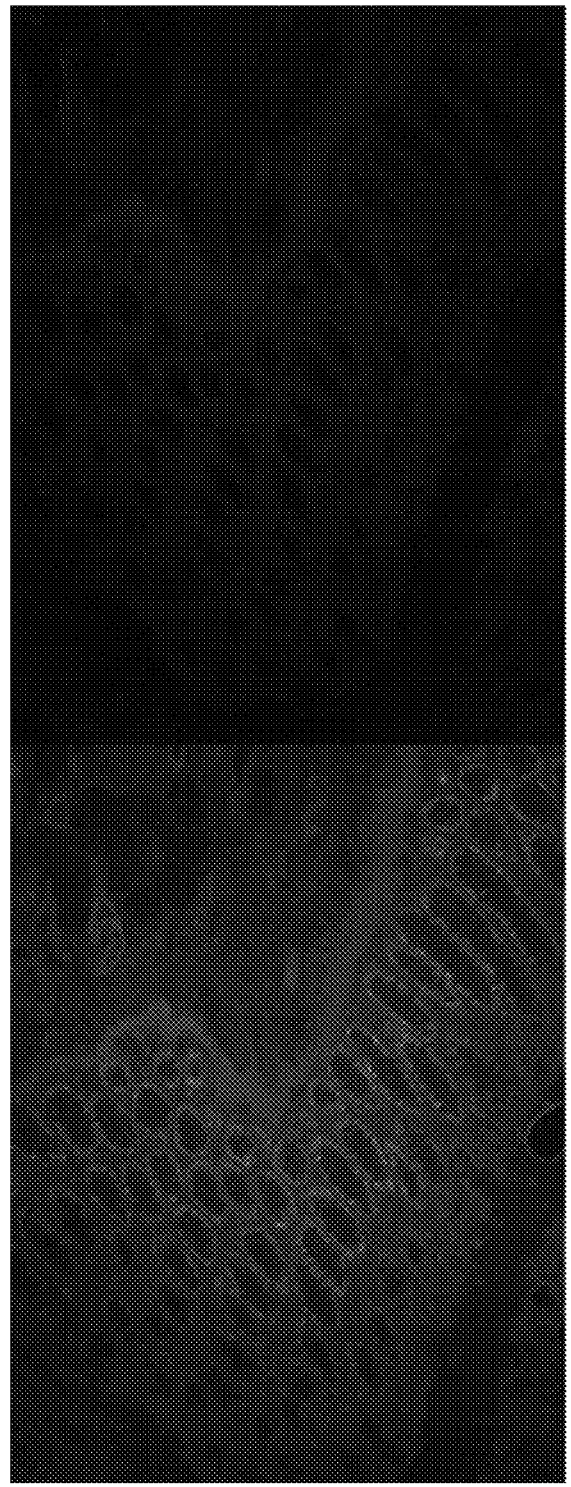
FIG. 12 depicts micrographs (at 10× magnification) of Sample 18a (before signal modification) and Sample 18b (after signal modification).

A normal colon slide was stained with a primary antibody mouse anti proliferating cell nuclear antigen (PCNA) clone pc 10, and targeted with a Cy3-conjugated donkey anti-mouse to form Sample 18a. Sample 18a was imaged and then treated with a NaOH solution to form Sample 18b, which was imaged again. Staining, imaging, and dye destruction steps were performed according to the procedures described hereinabove in Examples 8 and 9. FIG. 12 shows micrographs (at 10x magnification) of Sample 18a (before dye destruction) and Sample 18b (after dye destruction). After treatment with NaOH little or no signal from Cy3 remained.

Example 11

Single Channel Staining and Imaging of a Normal Colon Tissue using NaOH

Figure 13:
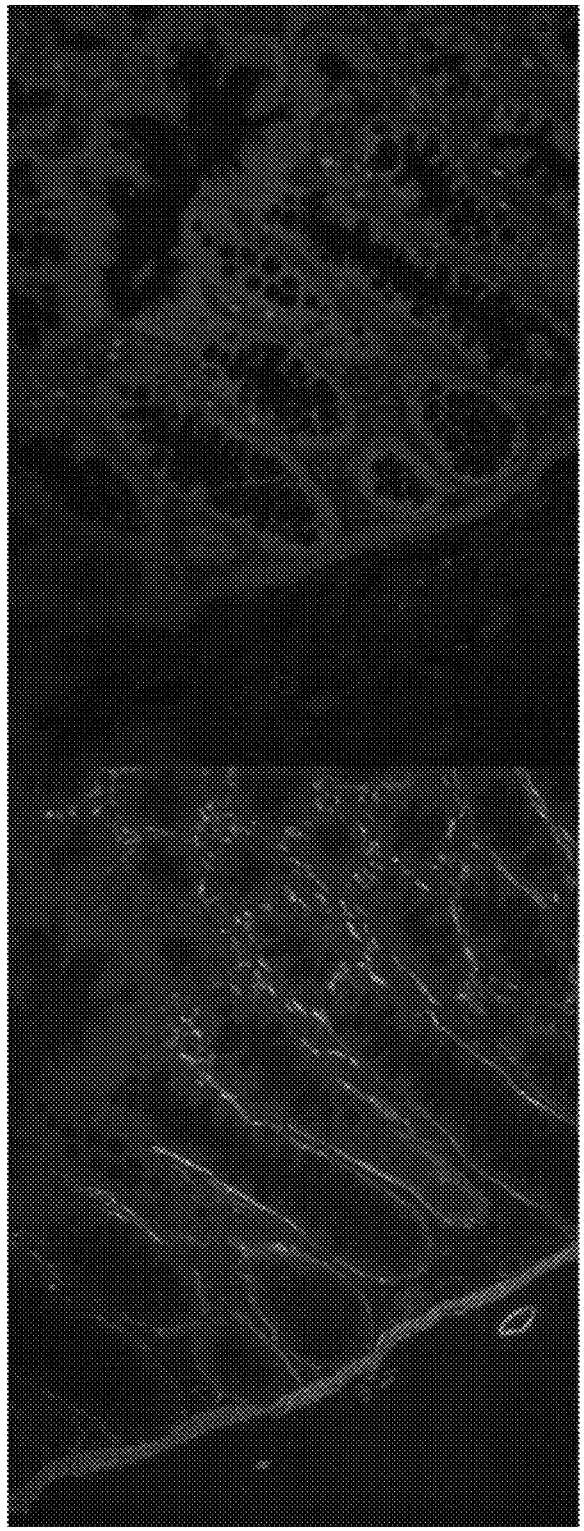
FIG. 13 depicts micrographs (at 10× magnification) of Sample 19a (before signal modification) and Sample 19b (after signal modification).

A normal colon slide was stained with a primary antibody mouse anti smooth muscle alpha actin (5 mA) clone 1A4, and targeted with a Cy3-conjugated donkey anti-mouse to form Sample 19a. Sample 19a was imaged and then treated with a NaOH solution to form Sample 19b, which was imaged again. Staining, imaging, and dye destruction steps were performed according to the procedures described hereinabove in Examples 8 and 9. FIG. 13 shows micrographs (at 10x magnification) of Sample 19a (before dye destruction) and Sample 19b (after dye destruction). After treatment with NaOH a little amount of signal from Cy3 remained.

Example 12

Two Channel Staining and Imaging of a Normal Breast Tissue Using NaOH

A normal breast tissue was stained with a primary antibody 5 mA, targeted with a Cy3-conjugated donkey anti-mouse, and counter-stained with DAPI to form Sample 20a. Sample 20a was imaged and then treated with a NaOH solution to form Sample 20b, which was imaged again. Staining, imaging, and dye destruction steps were performed according to the procedures described hereinabove in Examples 8 and 9. Sample 20b was restained with a primary antibody rabbit anti beta catenin, and targeted with a Cy3-conjugated anti-rabbit to form Sample 20c. Sample 20c was imaged and then counter-stained with H&E to form Sample 20d and imaged again.

Figure 14:
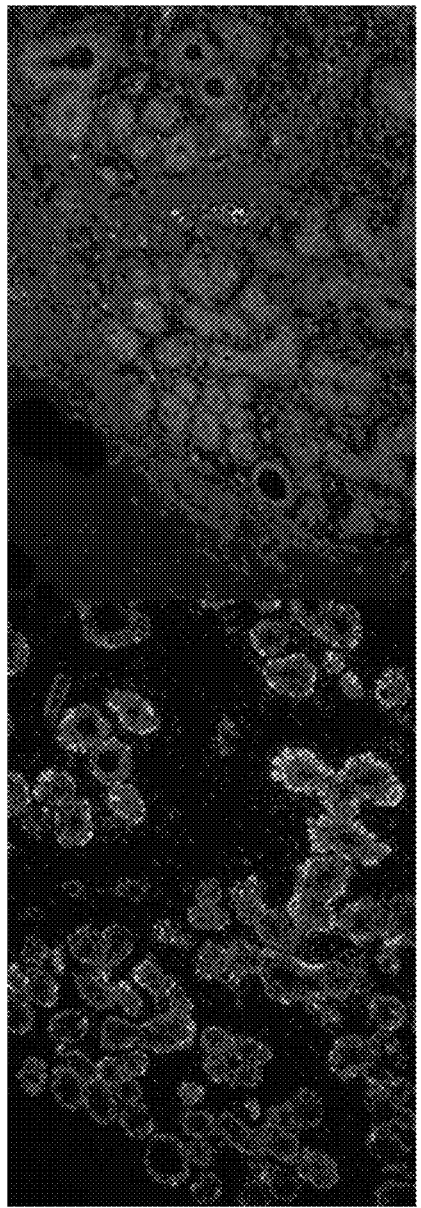
FIG. 14 depicts micrographs of Sample 20a (before signal modification) and Sample 20b (after signal modification).
Figure 14:
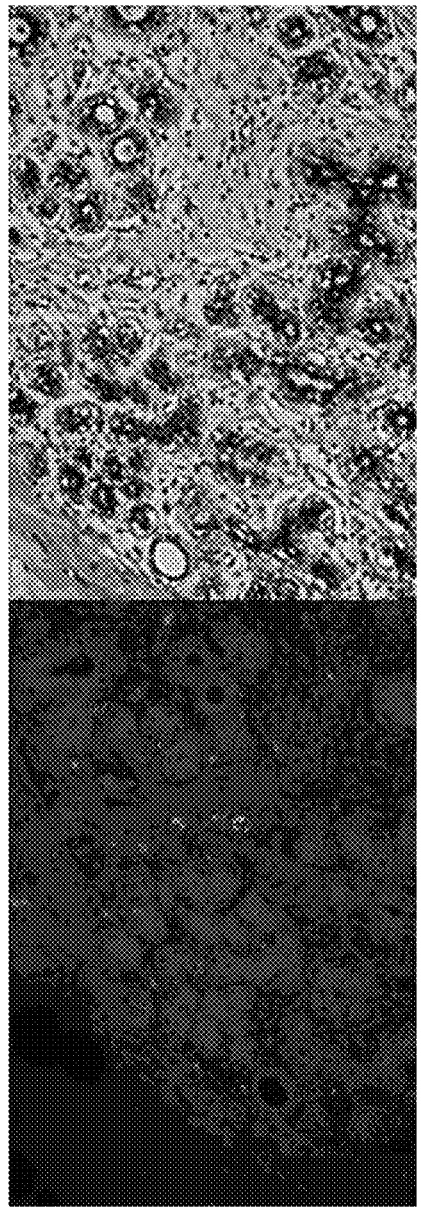

FIG. 14 shows micrographs of Sample 20a (before dye destruction) and Sample 20b (after dye destruction). After treatment with NaOH little or no signal from Cy3 remained and only DAPI was observed. Micrograph of Sample 20c showed imaging in the same Cy3 channel was possible by

Example 13

Two Channel Staining and Imaging of a Prostate Cancer Tissue Using NaOH

A prostate cancer tissue was stained with a primary antibody mouse anti pan cytokeratin clone PCK-26, and targeted with a Cy3-conjugated donkey anti-mouse, to form Sample 21a. Sample 21a was imaged and then counterstained with DAPI to form Sample 21b. Sample 21b was imaged and then treated with a NaOH solution to form Sample 21c, which was imaged again. Staining, imaging, and dye destruction steps were performed according to the procedures described hereinabove in Examples 8 and 9. Sample 21c was restained with a primary antibody 5 mA, and targeted with a Cy3-conjugated anti-rabbit to form Sample 21d and imaged again.

Figure 15:
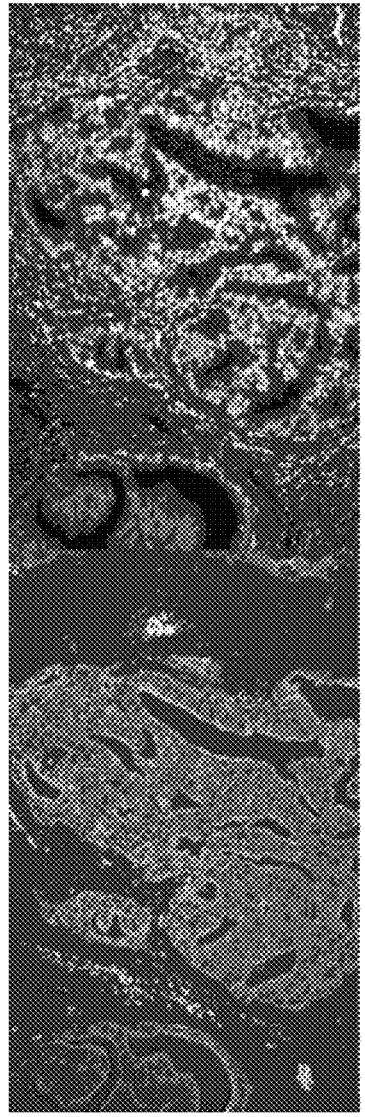
FIG. 15 depicts micrographs of Samples 21a and b (before signal modification) and Sample 21c (after signal modification).
Figure 15:
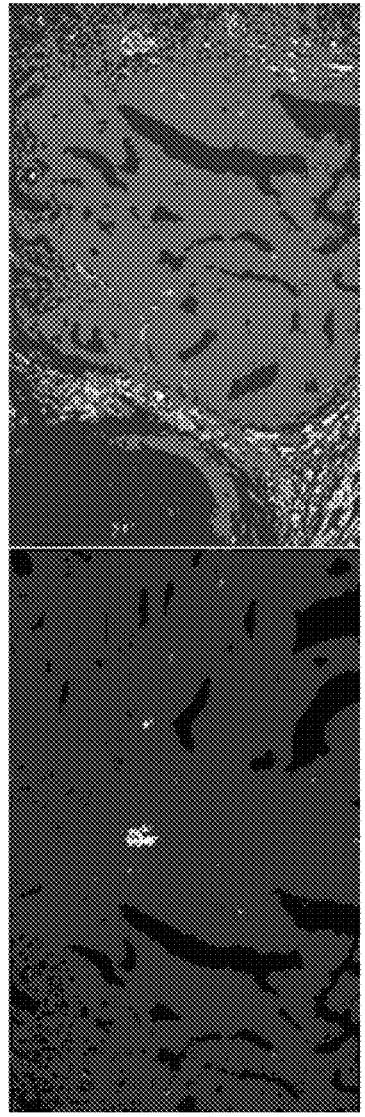

FIG. 15 shows micrographs of Samples 21a and b (before dye destruction) and Sample 21c (after dye destruction). After treatment with NaOH little or no signal from Cy3 remained and only DAPI was observed. Micrograph of Sample 21d showed imaging in the same Cy3 channel was possible by staining with a different antibody. Nuclear information about the tissue was obtained by staining with DAPI (Sample 21b).

Example 14

Two Channel Staining and Imaging of a Colon Adenocarcinoma Using NaOH

A colon adenocarcinoma slide was stained with a primary antibody mouse anti pan cytokeratin clone PCK-26, and targeted with a Cy3-conjugated donkey anti-mouse, to form Sample 22a. Sample 22a was imaged and then counterstained with DAPI to form Sample 22b. Sample 22b was imaged and then treated with a NaOH solution to form Sample 22c, which was imaged again. Staining, imaging, and dye destruction steps were performed according to the procedures described hereinabove in Examples 8 and 9. Sample 22c was restained with a primary antibody 5 mA, and targeted with a Cy3-conjugated anti-rabbit to form Sample 22d and imaged again.

Figure 16:
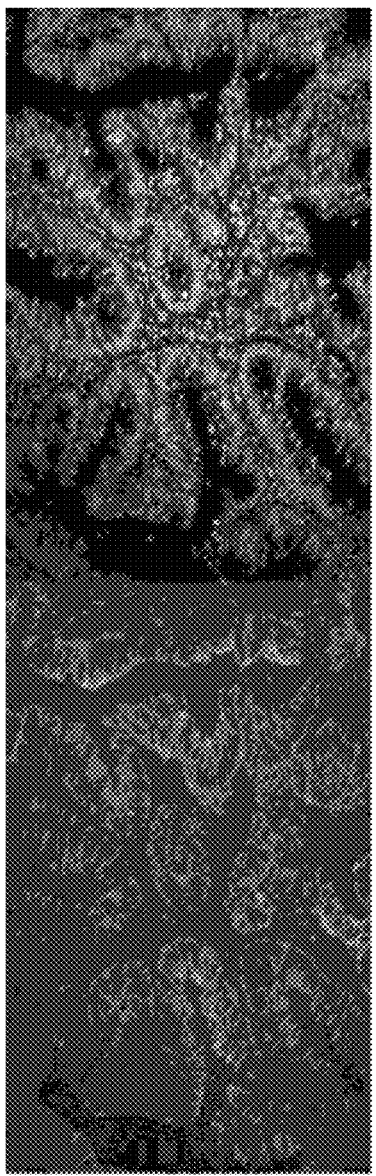
FIG. 16 depicts micrographs of Samples 22a and b (before signal modification) and Sample 22c (after signal modification).
Figure 16:
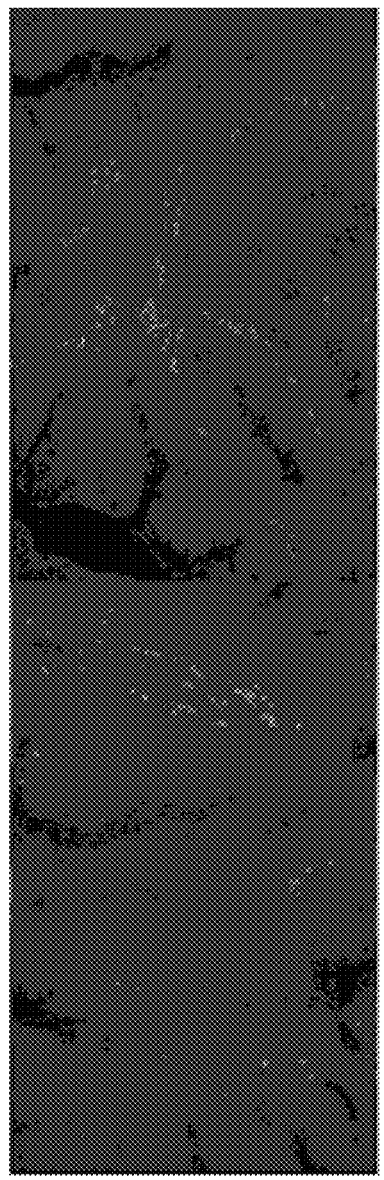

FIG. 16 shows micrographs of Samples 22a and b (before dye destruction) and Sample 22c (after dye destruction). After treatment with NaOH little or no signal from Cy3 remained and only DAPI was observed. Micrograph of Sample 22d showed imaging in the same Cy3 channel was possible by staining with a different antibody. Nuclear information about the tissue was obtained by staining with DAPI (Sample 22b).

Example 15

Two Channel Staining and Imaging of a Breast Tissue Microarray With Baseline Measurement Using NaOH A breast tissue microarray (Sample 23a) was imaged in the DAPI and Cy3 channel to measure the autofluorescence from the tissue. Sample 23a was then stained with DAPI to form Sample 23b, imaged and then treated with NaOH to form Sample 23c, and imaged again. Sample 23a was also stained with a primary antibody mouse anti estrogen receptor alpha clone 1D5, and targeted with a Cy3-conjugated donkey anti-mouse, to form Sample 23d. Sample 23d was imaged then treated with a NaOH solution to form Sample 23e, which was imaged again. Staining, imaging, and dye destruction steps were performed according to the procedures described hereinabove in Examples 8 and 9.

Figure 17:
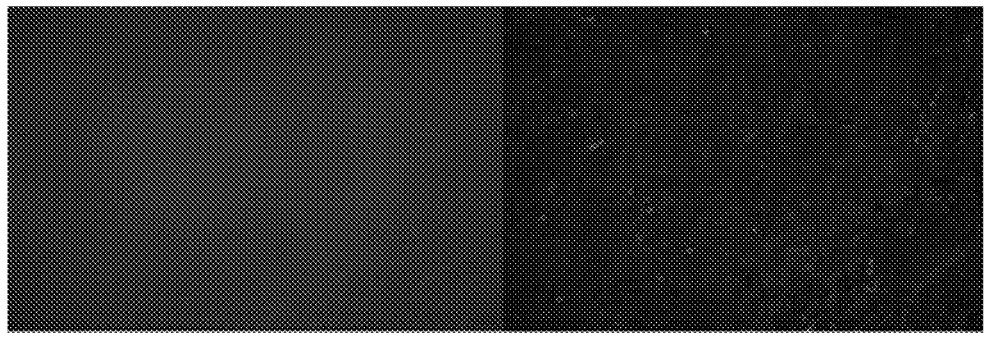
FIG. 17 depicts micrographs of Samples 23a-e.
Figure 17:
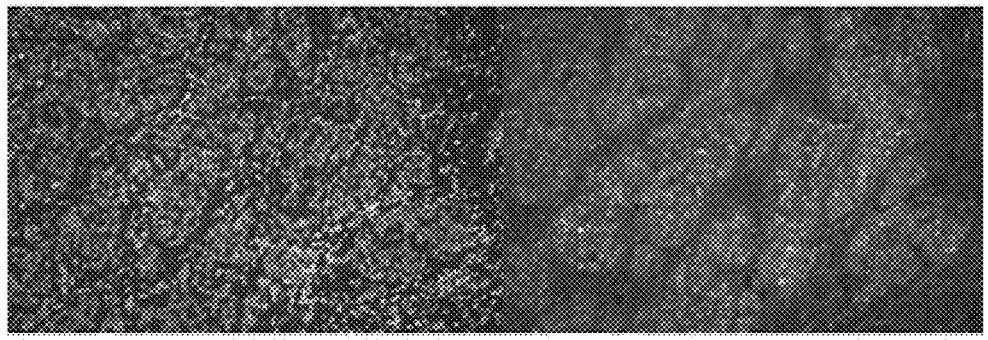
Figure 17:
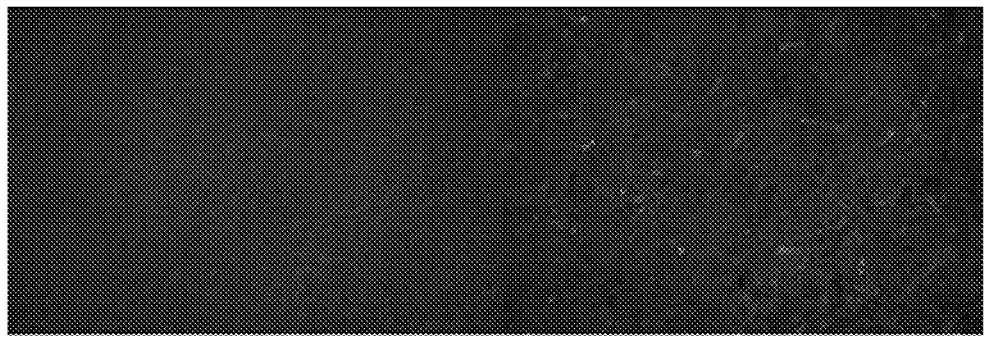

FIG. 17 shows micrographs of Samples 23a-e. Micrographs of Samples 23c and 23e were compared to the autofluorescence (baseline) observed in Sample 23a. Both Samples showed signal reduction. DAPI-stained sample showed signal reduction possibly due to destruction of nucleic acids to which DAPI binds.

Example 16

Three Channel Staining and Imaging of Breast TMA using NaOH

A breast TMA slide was stained with a primary antibody mouse anti pan cytokeratin clone PCK-26, targeted with a Cy3-conjugated donkey anti-mouse, and counterstained with DAPI to form Sample 24a. Sample 24a was imaged and then treated with a NaOH solution to form Sample 24b, which was imaged again. Staining, imaging, and dye destruction steps were performed according to the procedures described hereinabove in Examples 8 and 9. Sample 24b was restained with a Cy3-directly conjugated beta catenin antibody to form Sample 24c and imaged again. The array was again treated with NaOH and labeled with Cy3-direct conjugated 5 mA antibody to form Sample 24d and imaged again. The images obtained were registered, pseudo colored and overlaid (Sample 24e) to give spatial information for expressing antigen. Sample 24d was further stained with H&E to form Sample 24f.

Figure 18:
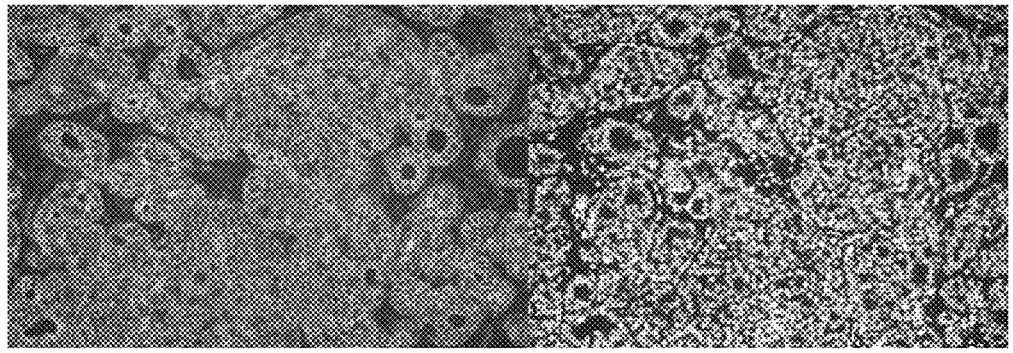
FIG. 18 depicts micrographs of Sample 24a (before signal modification) and Sample 24b (after signal modification).
Figure 18:
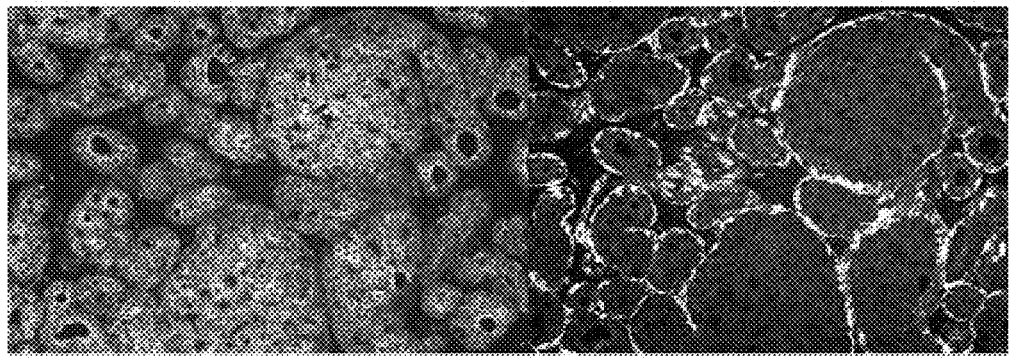
Figure 18:
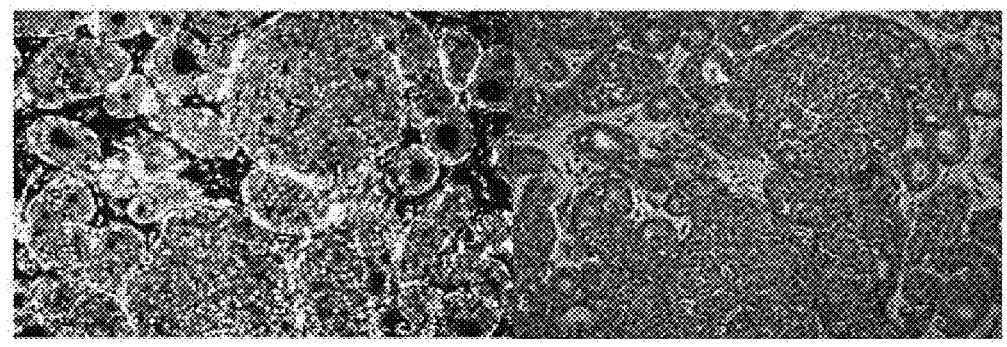

FIG. 18 shows micrographs of Sample 24a (before dye destruction) and Sample 24b (after dye destruction). After treatment with NaOH little or no signal from Cy3 remained and only DAPI was observed. Micrographs of Samples 24c and 24d showed imaging in the same Cy3 channel was possible by staining with different antibodies. Morphological information about the tissue was obtained by staining with H&E (Sample 24f).

Example 17

Twelve Channel Staining and Imaging of Normal Prostate Using NaOH

Images were taken prior to staining to baseline the autofluorescence coming from each channel. A normal prostate slide was stained with a cocktail of primary antibodies: mouse anti pan cytokeratin clone and goat anti vimentin. The two primary antibodies were targeted with a second cocktail of secondary antibodies Cy3-conjugated donkey anti-mouse and Cy5-conjugated donkey anti-goat to form Sample 25a. Sample 25a was imaged and then treated with a NaOH solution. The tissue was then stained with a second cocktail of primary antibodies: androgen receptor clone and alpha catenin The two primary antibodies were targeted with another cocktail of Cy-3 and Cy-5 conjugated secondary antibodies to form Sample 25b. Sample 25b was imaged and then treated with a NaOH solution. This was followed by staining-imaging-NaOH treatment-staining steps using seven Cy-directly conjugated antibodies (Samples 25c-25i). The antibodies used were: smooth muscle alpha actin, beta catenin, pan cadherin, Von willebrand factor 7, keratin 5, keratin 8/18, and e-cadherin. Each staining step included counterstaining with DAPI (Sample 25j).

Figure 19:
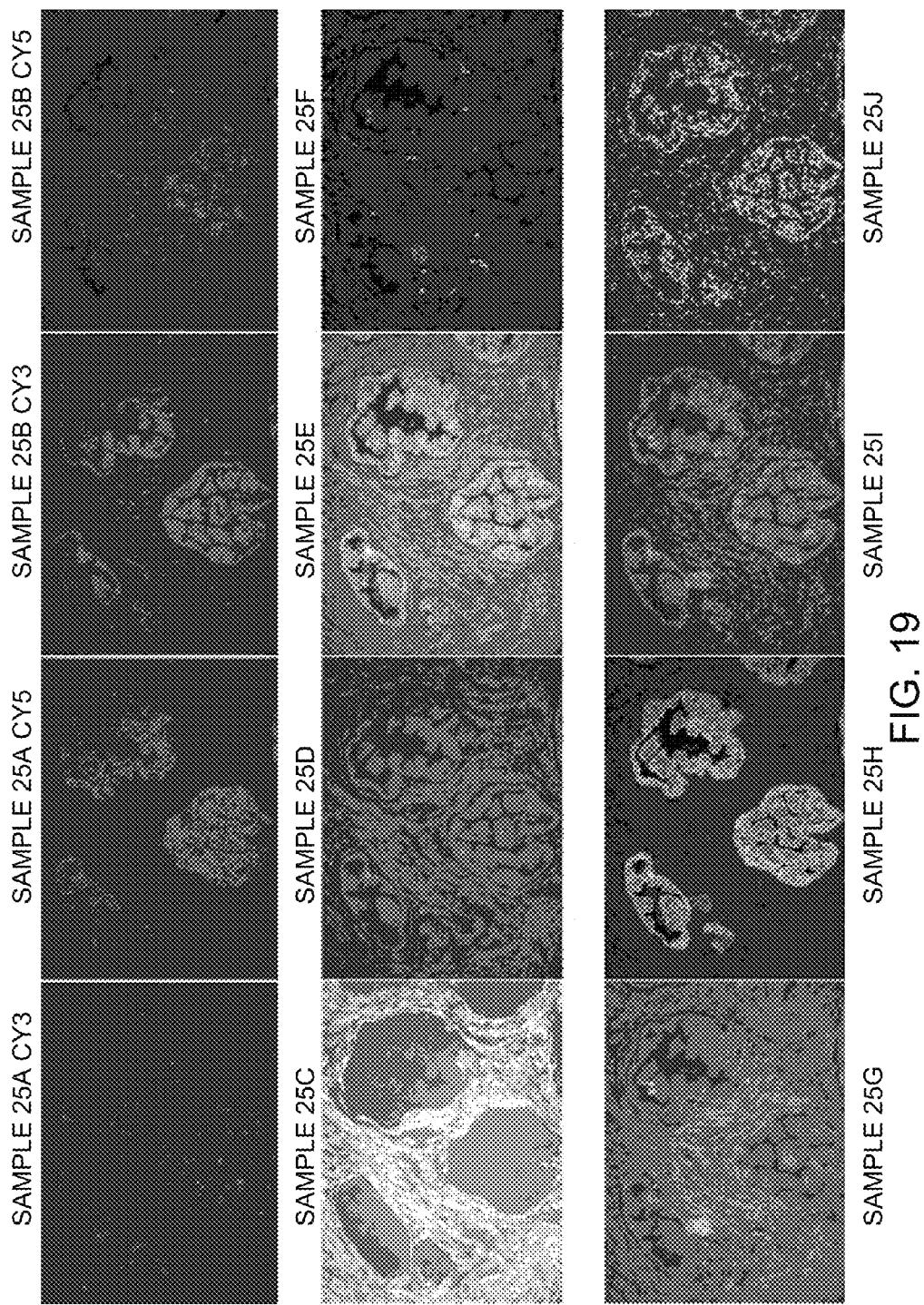
FIG. 19 depicts micrographs of Sample 25a (Cy3 and Cy5 channels), Sample 25b (Cy3 and Cy5 channels), and Samples 25c-25j.

FIG. 19 shows micrographs of Sample 25a (Cy3 and Cy5 channels), Sample 25b (Cy3 and Cy5 channels), and Samples 25c-25j. FIG. 19 shows that multiple imaging in the same Cy3 channel was possible by staining with different antibodies. 12-channel multiple imaging was possible with 9 of the channels being Cy3 channels.

Example 18

Four Channel Staining and Imaging of Normal Prostrate Using $H_2O_2$

Images were taken prior to staining to baseline the autofluorescence coming from each channel. A normal prostrate slide was stained with a Cy3-directly conjugated pan cadherin to form Sample 26a. The slide was imaged and treated with H2O2 (Sample 26b), restained with Cy3-conjugated SmA (Sample 26c), treated with $H_2O_2$ (Sample 26d), restained with Cy3-conjugated pan cytokeratin (Sample 26e), treated with $H_2O_2$ (Sample 26f), restained with Cy-conjugated vimentin (Sample 26g), and treated with $H_2O_2$ (Sample 26g).

Figure 20:
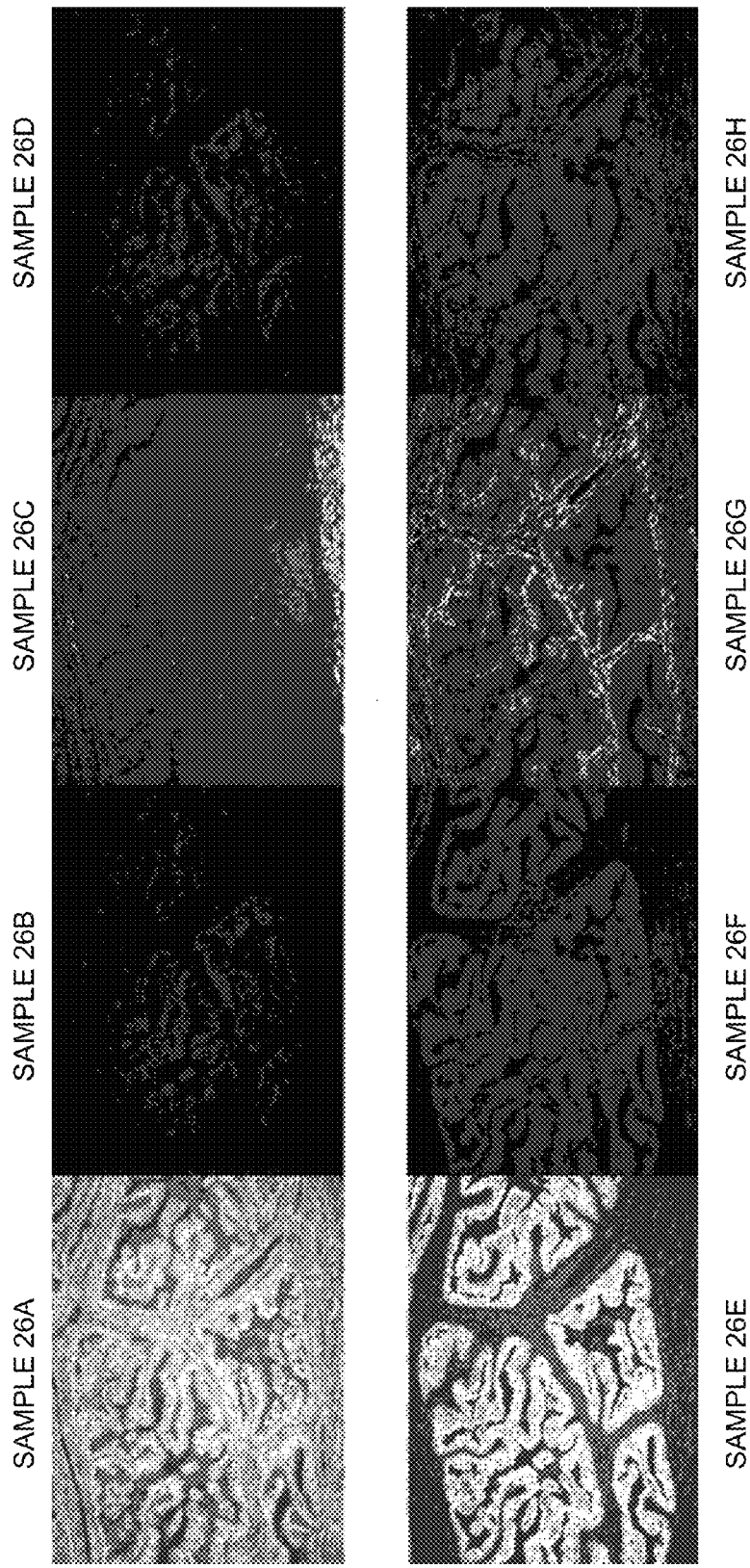
FIG. 20 depicts micrographs of Samples 26a-h.

FIG. 20 shows micrographs of Samples 26a-g. FIG. 20 shows that multiple imaging in the same Cy3 channel was possible by staining with different antibodies and destroying the signal using $H_2O_2$.

Example 19

Residual Stain Following Staining for Abundant Proteins Using NaOH

Figure 21:
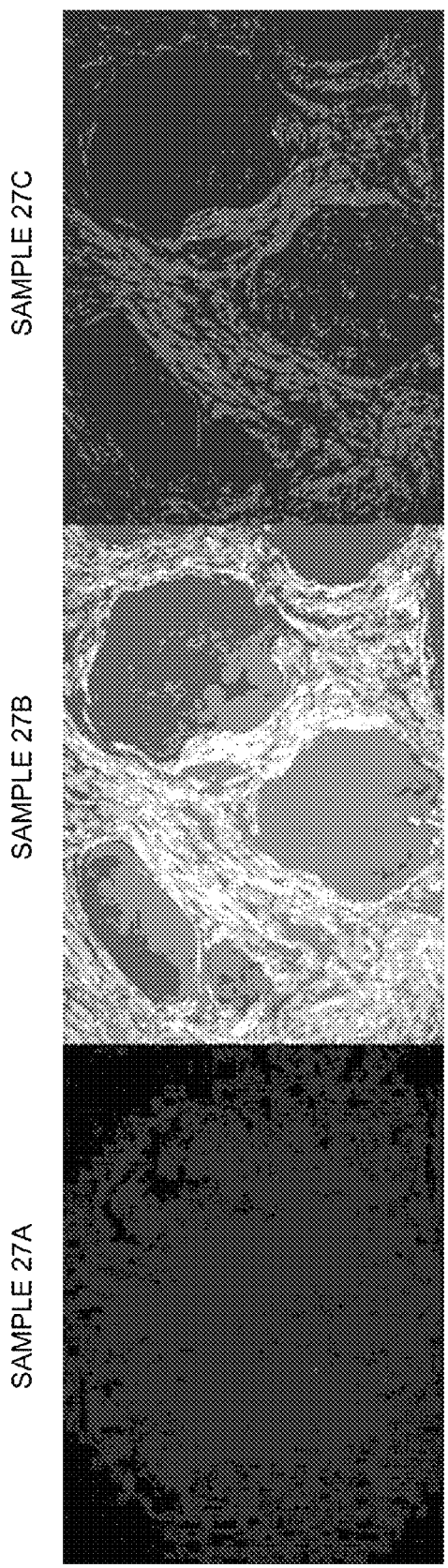
FIG. 21 depicts the micrographs of Samples 27-c.

A normal prostrate (Sample 27a) was imaged in the Cy3 channel to measure the autofluorescence from the tissue. Sample 27a was then stained with Cy3-conjugated 5 mA to form Sample 27b, imaged and then treated with NaOH to form Sample 27c, and imaged again. Staining, imaging, and dye destruction steps were performed according to the procedures described hereinabove in Examples 8 and 9. FIG. 21 shows the micrographs of Samples 27a-C. Residual stain was observed post NaOH treatment.

Figure 22:
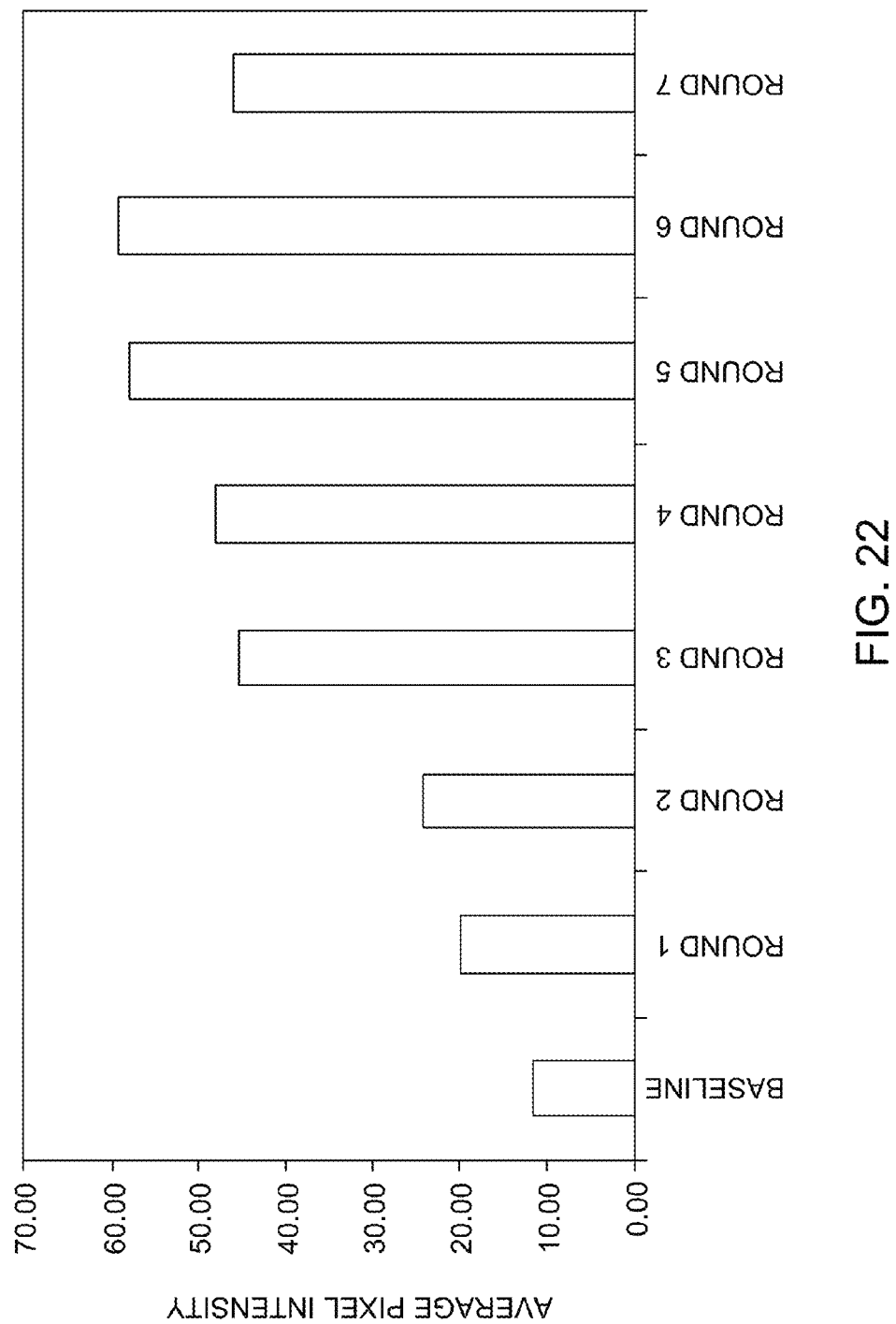
FIG. 22 is a plot of average pixel intensity of the background for each cycle in the imaging in Example 20.

Residual stain values were also monitored during the twelve channels multiple imaging described in Example 17. Using Gimp 2.2, average pixel intensities were collected for each background and NaOH treated image and tabulated. FIG. 22 shows a plot of average pixel intensity of the background for each cycle in the imaging as well as a small image of what the background looked like prior to staining. A large spike in residual stain intensity was observed in cycle 4 as 5 mA, an abundantly expressed protein was stained in cycle 3.

Example 20

Residual Stain Following Staining for Abundant Proteins Using NaOH and $H_2O_2$ Treatment Two prostate slides were stained with Cy3-directly conjugated 5 mA (Samples 28a and 28b). Both slides were given identical pretreatment steps, concentrations, antigen retrieval and the only difference was signal-destruction method: method-one being with NaOH (Sample 28c), the other with $H_2O_2$ (Sample 28d). Two other prostate slides were stained with Cy3-directly conjugated pan cadherin (Samples 29a and 29b). Both slides were given identical pretreatment steps, concentrations, antigen retrieval and the only difference was signal-destruction method; method-one being with NaOH (Sample 29c), the other with $H_2O_2$ (Sample 29d).

Figure 23:
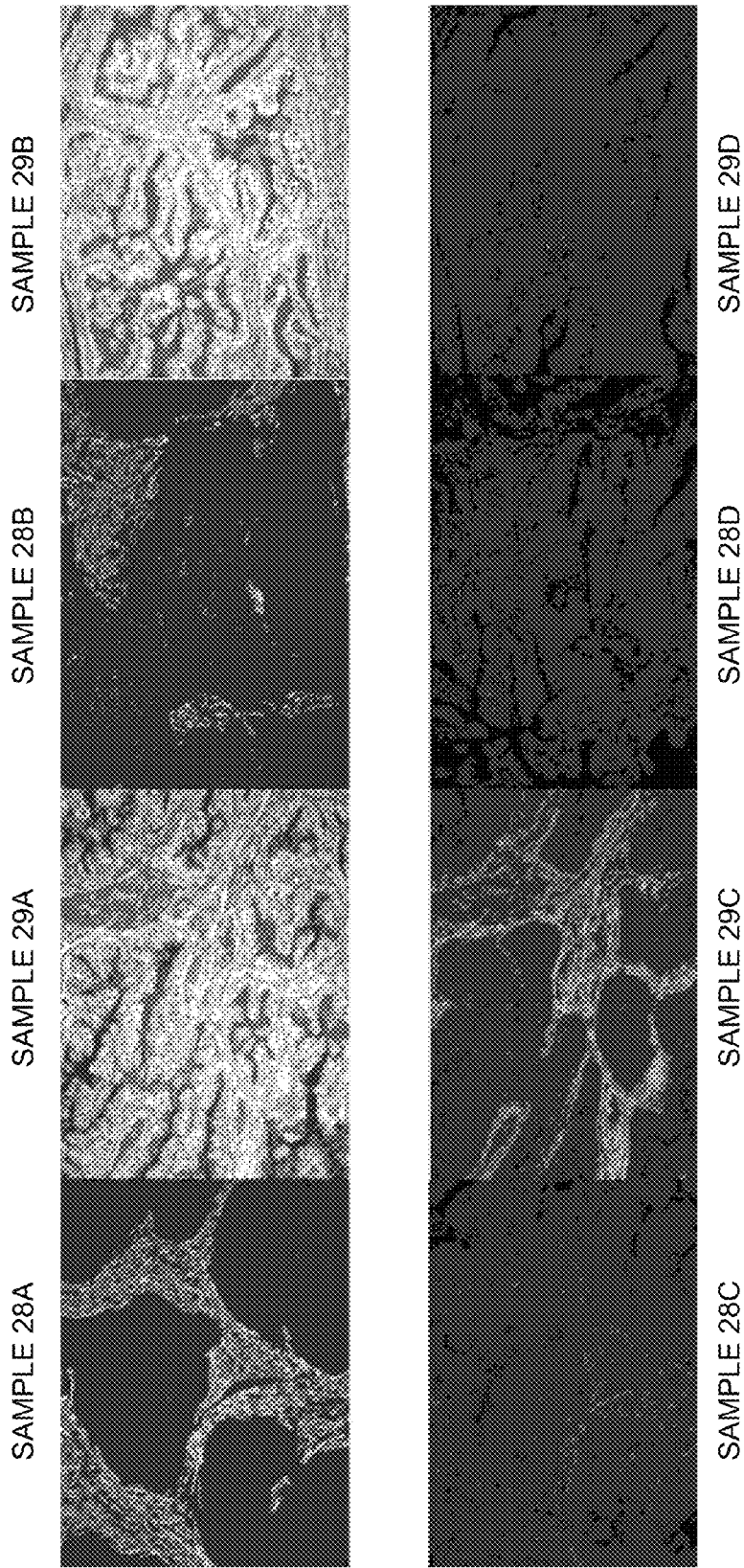
FIG. 23 shows comparison between micrographs of Samples 28-c and 29a-c.

FIG. 23 shows head to head micrographs of 5 mA and pan cadherin staining and signal removal. $H_2O_2$ showed more efficient dye removal for both 5 mA and pan cadherin when compared to NaOH.

Example 21

Residual Stain Following Multiple Cycle Staining for Abundant Proteins Using NaOH and $H_2O_2$ Treatment Two prostate slides were stained with Cy3-directly conjugated 5 mA (Samples 30a and 30b). Both slides were given identical pretreatment steps, concentrations, antigen retrieval and the only difference was signal-destruction method; method-one being with NaOH (Sample 30c), the other with $H_2O_2$ (Sample 30d). The slides were subjected to 9 staining and signal-destruction cycles before staining with Cy3-conjugated pan cytokeratin.

Figure 24:
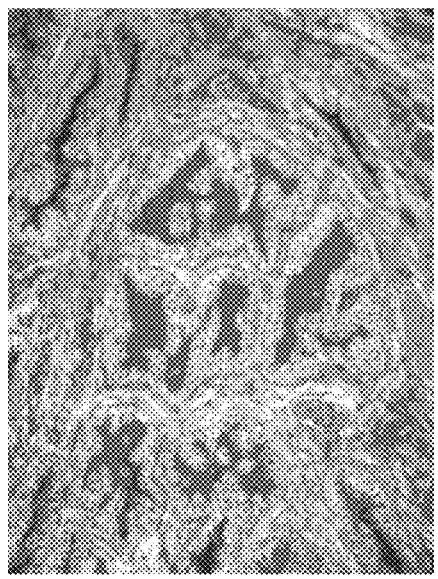
FIG. 24 depicts micrographs of Samples 30a-d.
Figure 24:
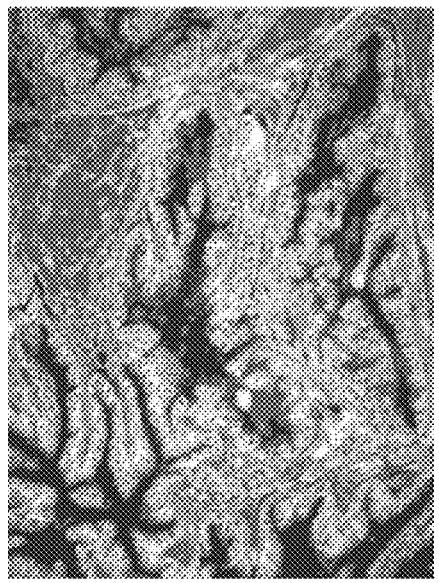
Figure 24:
Figure 24:
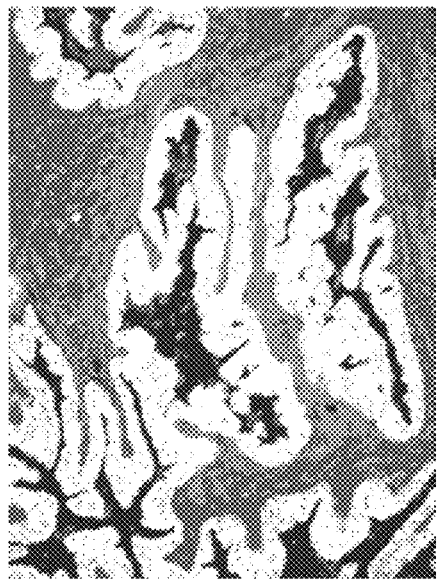
Figure 25:
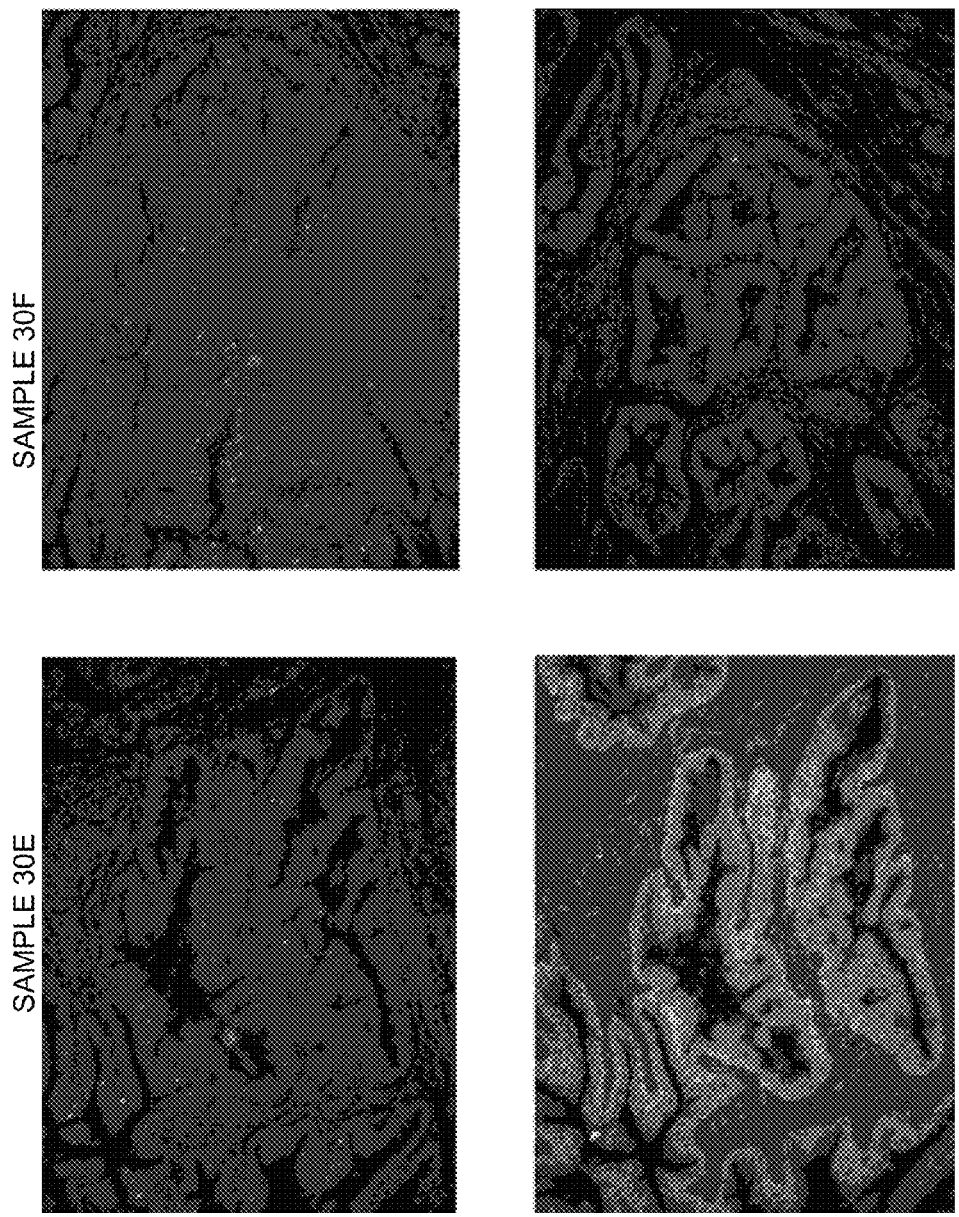
FIG. 25 depicts micrographs of Samples 30c-f
Figure 26:
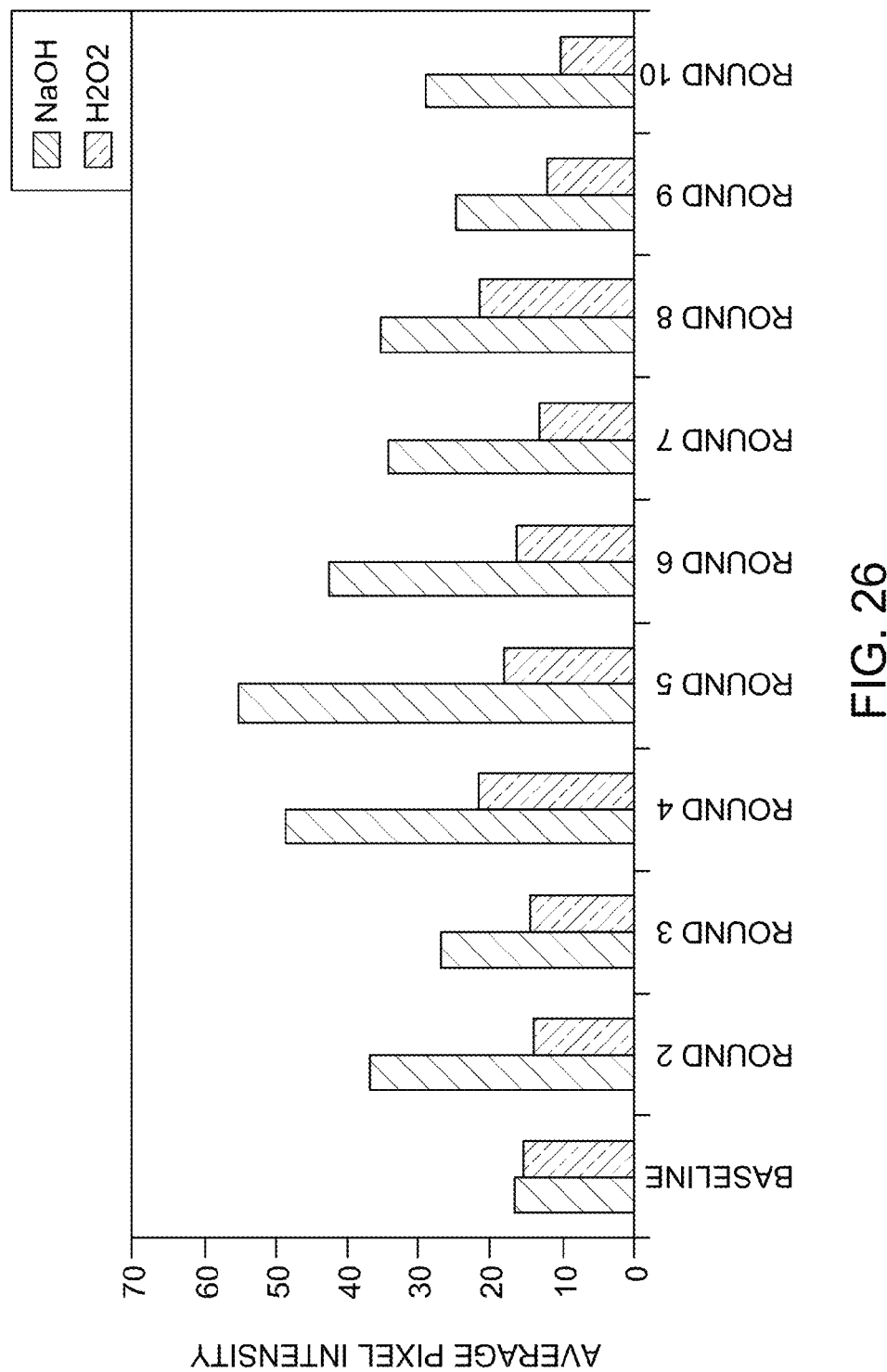
FIG. 26 is a plot of average pixel intensities for the background of each cycle for Samples 30c and 30d.

FIG. 24 compares staining from first cycle pan cadherin stain to the $9^{th}$ cycle of pan cytokeratin using NaOH and $H_2O_2$ to destroy the signal after each staining $H_2O_2$ showed more efficient dye removal after 9 cycles when compared to NaOH. FIG. 25 compares background from unstained samples (Samples 30e and 30f) and after 9 cycles of NaOH and $H_2O_2$ treatment (Samples 30c and 30d). $H_2O_2$ showed more efficient dye removal for both 5 mA and pan cadherin when compared to NaOH. FIG. 26 is a plot of average pixel intensities for the background of each cycle for the NaOH and $H_2O_2$ slides. The background for the $H_2O_2$ slide was significantly less for each cycle after the initial baseline. Below each cycle is also a small image of each background with the NaOH background image on top and $H_2O_2$ background image on bottom.

Example 22

Antibody Stability to Chemical Agents

Figure 27:
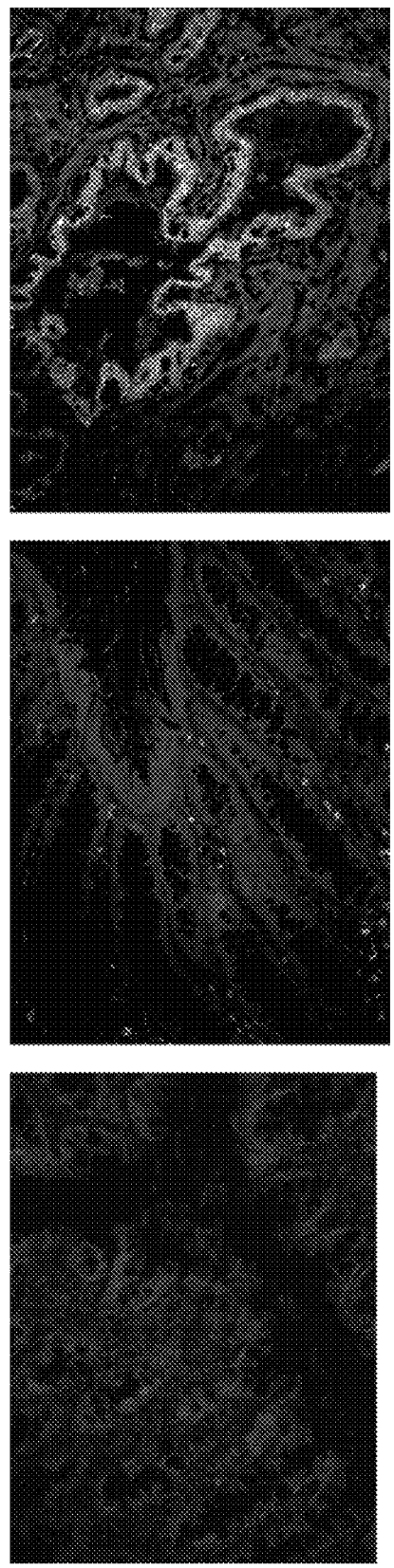
FIG. 27 depicts micrographs of Samples 31a, 31b, and 31c.

A colon tissue slide was stained with a primary antibody rabbit anti beta catenin and targeted with a Cy3-conjugated donkey anti-rabbit secondary antibody to form Sample 31a. Sample 31a was imaged and then treated with a NaOH solution to form Sample 31b, which was imaged again. Staining, imaging, and dye destruction steps were performed according to the procedures described hereinabove in Examples 8 and 9. Sample 31b was restained with a Cy3-conjugated anti rabbit secondary antibody to form Sample 31c and imaged again. FIG. 27 shows micrographs of Samples 31a-c. FIG. 27 shows that the primary antibody remains bound to the sample after NaOH treatment.

Figure 28:
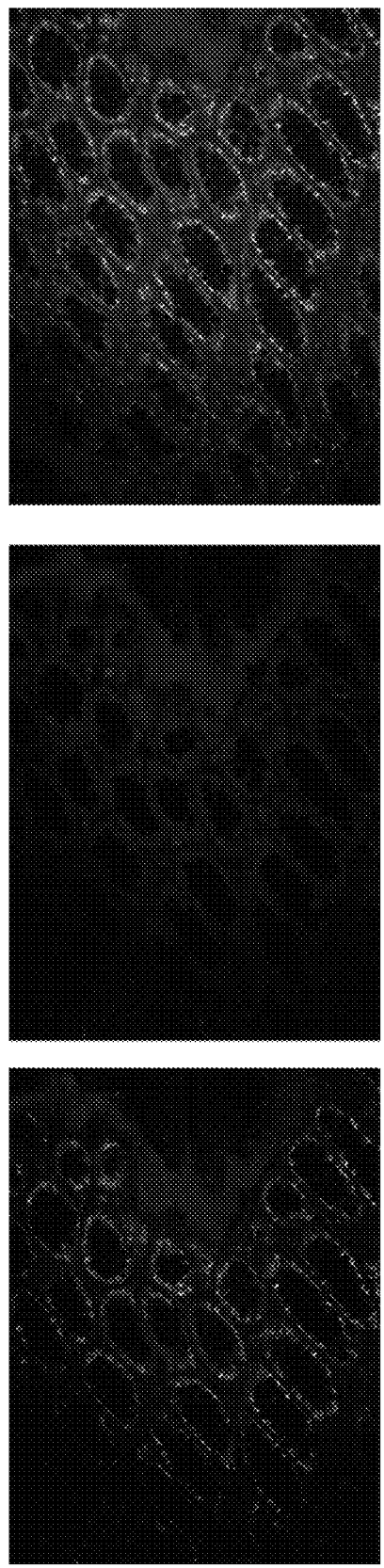
FIG. 28 depicts micrographs of Samples 32a, 32b, and 32c.

A colon tissue slide was stained with a primary antibody mouse-anti PCNA and targeted with a Cy3-conjugated donkey anti-mouse secondary antibody to form Sample 32a. Sample 31a was imaged and then treated with a NaOH solution to form Sample 32b, which was imaged again. Staining, imaging, and dye destruction steps were performed according to the procedures described in Examples 8 and 9. Sample 32b was restained with a Cy3-conjugated anti-mouse secondary antibody to form Sample 32c and imaged again. FIG. 28 shows that the primary antibody is still bound to the sample after treatment with NaOH.

The invention may be embodied in other specific forms without departing from the spirit or essential characteristics thereof. The foregoing embodiments are thereof to be considered in all respects illustrative rather than limiting on the invention described herein. Scope of the invention is thus indicated by the appended claims rather than by the foregoing description, and all changes that come within the meaning and range of equivalency of the claims are therefore intended to be embraced therein.

The invention claimed is:

1. A method of detecting multiple targets in a biological sample, comprising:
   (a) contacting the biological sample with a first plurality of probes capable of binding a first group of different targets in the biological sample;
   (b) binding the first plurality of probes to their respective targets;
   (c) detecting signals from the first plurality of probes;
   (d) applying an oxidizing agent after step (c) to modify the signals;
   (e) contacting the biological sample after step (d) with a second plurality of probes capable of binding a second group of different targets in the biological sample;
   (f) binding the second plurality of probes to their respective targets; and
   (g) detecting signals from the second plurality of probes; and
   wherein each probe comprises an antibody and a fluorophore.

2. The method of claim 1, wherein the oxidizing agent is hydrogen peroxide.

3. The method of claim 1, wherein the biological sample comprises a tissue section.

* * * * *

UNITED STATES PATENT AND TRADEMARK OFFICE
CERTIFICATE OF CORRECTION

| | |
|---|---|
| PATENT NO. | : 8,822,147 B2 |
| APPLICATION NO. | : 13/457531 |
| DATED | : September 2, 2014 |
| INVENTOR(S) | : Sood et al. |

It is certified that error appears in the above-identified patent and that said Letters Patent is hereby corrected as shown below:

On the Title Page, item (75), under "Inventors", in Column 1, Line 3, delete "Michael Gerdes," and insert -- Michael John Gerdes, --, therefor.

In the Specification

In Column 2, Line 57, delete "27-c." and insert -- 27a-c. --, therefor.

In Column 2, Line 61, delete "28-c" and insert -- 28a-c --, therefor.

In Column 2, Line 63, delete "30c-f" and insert -- 30c-f. --, therefor.

In Column 5, Line 54, delete "lathanide" and insert -- lanthanide --, therefor.

In Column 7, Line 54, delete "prostrate." and insert -- prostate. --, therefor.

In Column 11, Line 48, delete "interactions," and insert -- hydrophobic interactions, --, therefor.

In Column 12, Line 63, delete "(IHC)" and insert -- (IHC). --, therefor.

In Column 13, Line 48, delete "salvary," and insert -- salivary, --, therefor.

In Column 13, Line 57, delete "(5 mA)," and insert -- (SmA), --, therefor.

In Column 15, Line 41, delete "anti-H isG" and insert -- anti-HisG --, therefor.

In Column 17, Line 43, delete "$^{14}C$, $^{125}I$ and $^{131}I$)," and insert -- $C^{14}$, $I^{125}$ and $I^{131}$), --, therefor.

In Column 18, Line 26, delete "dip yrromethene" and insert -- dipyrromethene --, therefor.

Signed and Sealed this
Twentieth Day of January, 2015

Michelle K. Lee
*Deputy Director of the United States Patent and Trademark Office*

In Column 18, Line 32, delete "(1R)" and insert -- (IR) --, therefor.

In Column 19, Line 25, delete "((3-D-Gal)" and insert -- (β-D-Gal) --, therefor.

In Column 30, Line 27, delete "prostrate" and insert -- prostate --, therefor.

In Column 30, Line 62, delete "(5 mA)," and insert -- (SmA), --, therefor.

In Column 31, Line 9, delete "column The" and insert -- column. The --, therefor.

In Column 32, Line 35, delete "(5 mA)" and insert -- (SmA) --, therefor.

In Column 32, Line 52, delete "5 mA," and insert -- SmA, --, therefor.

In Column 33, Line 7, delete "Prostrate" and insert -- Prostate --, therefor.

In Column 33, Line 10, delete "prostrate" and insert -- prostate --, therefor.

In Column 33, Line 19, delete "5 mA," and insert -- SmA, --, therefor.

In Column 33, Line 43, delete "5 mA," and insert -- SmA, --, therefor.

In Column 34, Line 26, delete "5 mA" and insert -- SmA --, therefor.

In Column 34, Line 44, delete "Prostrate" and insert -- Prostate --, therefor.

In Column 34, Line 47, delete "prostrate" and insert -- prostate --, therefor.

In Column 34, Lines 55-56, delete "catenin The" and insert -- catenin. The --, therefor.

In Column 35, Line 9, delete "Prostrate" and insert -- Prostate --, therefor.

In Column 35, Line 12, delete "prostrate" and insert -- prostate --, therefor.

In Column 35, Line 32, delete "prostrate" and insert -- prostate --, therefor.

In Column 35, Line 34, delete "5 mA" and insert -- SmA --, therefor.

In Column 35, Line 39, delete "27a-C." and insert -- 27a-c. --, therefor.

In Column 35, Lines 49-50, delete "5 mA," and insert -- SmA, --, therefor.

In Column 35, Line 58, delete "5 mA" and insert -- SmA --, therefor.

In Column 36, Line 1, delete "5 mA" and insert -- SmA --, therefor.

CERTIFICATE OF CORRECTION (continued)
U.S. Pat. No. 8,822,147 B2

In Column 36, Line 3, delete "5 mA" and insert -- SmA --, therefor.

In Column 36, Line 13, delete "5 mA" and insert -- SmA --, therefor.

In Column 36, Line 27, delete "5 mA" and insert -- SmA --, therefor.